United States Patent
Kalled et al.

(10) Patent No.: US 11,111,307 B2
(45) Date of Patent: *Sep. 7, 2021

(54) ANTI-BCMA ANTIBODIES

(71) Applicant: Biogen MA Inc., Cambridge, MA (US)

(72) Inventors: Susan L. Kalled, Concord, MA (US); Yen-Ming Hsu, Lexington, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/026,242

(22) Filed: Jul. 3, 2018

(65) Prior Publication Data

US 2019/0161552 A1 May 30, 2019

Related U.S. Application Data

(63) Continuation of application No. 15/065,641, filed on Mar. 9, 2016, now abandoned, which is a continuation of application No. 14/596,769, filed on Jan. 14, 2015, now abandoned, which is a continuation of application No. 13/255,610, filed as application No. PCT/US2010/026825 on Mar. 10, 2010, now Pat. No. 9,034,324.

(60) Provisional application No. 61/162,924, filed on Mar. 24, 2009, provisional application No. 61/158,942, filed on Mar. 10, 2009.

(51) Int. Cl.
*C07K 16/28* (2006.01)
*A61K 39/00* (2006.01)

(52) U.S. Cl.
CPC .... *C07K 16/2878* (2013.01); *A61K 2039/505* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,225,539 A | 7/1993 | Winter | |
| 5,648,237 A | 7/1997 | Carter | |
| 5,736,137 A | 4/1998 | Anderson et al. | |
| 6,475,987 B1 | 11/2002 | Shu | |
| 6,632,927 B2 | 10/2003 | Adair et al. | |
| 7,083,785 B2 | 8/2006 | Browning et al. | |
| 7,112,421 B2 | 9/2006 | Ambrose et al. | |
| 7,371,388 B1 | 5/2008 | Ruben et al. | |
| 2003/0012783 A1 | 1/2003 | Kindsvogel | |
| 2005/0163775 A1 | 7/2005 | Chan et al. | |
| 2006/0067933 A1 | 3/2006 | Gross et al. | |
| 2006/0073146 A1 | 4/2006 | Ashkenazi et al. | |
| 2006/0084055 A1 | 4/2006 | Gaiger et al. | |
| 2006/0286093 A1 | 12/2006 | Gross et al. | |
| 2007/0086979 A1 | 4/2007 | Chevrier et al. | |
| 2007/0185017 A1 | 8/2007 | Aggarwal et al. | |

FOREIGN PATENT DOCUMENTS

| | | |
|---|---|---|
| EP | 1 798 243 A2 | 6/2007 |
| JP | 2004-533997 A | 11/2004 |
| JP | 2007-309746 A | 11/2007 |
| WO | WO 2000/040716 | 7/2000 |
| WO | WO 2000/068378 | 11/2000 |
| WO | WO 2001/060397 A1 | 8/2001 |
| WO | WO 2002/066516 A2 | 8/2002 |
| WO | WO 2003/013582 A1 | 2/2003 |
| WO | WO 2003/062401 A2 | 7/2003 |
| WO | WO 2003/072713 A2 | 9/2003 |
| WO | WO 2003/074566 A2 | 9/2003 |
| WO | WO 2004/039956 A2 | 5/2004 |
| WO | WO 2005/000351 A2 | 1/2005 |
| WO | WO 2006/068867 A1 | 6/2006 |
| WO | WO 2007/019618 A1 | 2/2007 |
| WO | WO 2007/070538 A2 | 6/2007 |
| WO | WO 2008/112017 A2 | 9/2008 |

OTHER PUBLICATIONS

Avery et al., "BAFF selectively enhances the survival of plasmablasts generated from human memory B Cells," *J. Clin. Invest.* 112:286-297 (2003).
Bellucci et al., "Graft-versus-tumor response in patients with multiple myeloma is associated with antibody response to BCMA, a plasma-cell membrane receptor," *Blood* 105(10):3945-3950 (2005).
Better et al., "*Escherichia coli* Secretion of an Active Chimeric Antibody Fragment," *Science* 240:1041-1043 (1988).
Brehm et al., "Parameters for establishing humanized mouse models to study human immunity: Analysis of human hematopoietic stem cell engraftment in three immunodeficient strains of mice bearing the IL2rγnull mutation," *Clin. Immunol.* 135(1):84-98 (2010).
Brezinsky et al., "A simple method for enriching populations of transfected CHO cells for cells of higher specific productivity," *J. Immunol. Methods* 277:141-155 (2003).
Casset et al., "A peptide mimetic of an anti-CD4 monoclonal antibody by rational design," *Biochem. Biophys. Res. Commun.* 307:198-205 (2003).
Chapoval et al. "Anti-CD3 x Anti-Tumor F(ab')$_2$ Bifunctional Antibody Activates and Retargets Tumor-Infiltrating Lymphocytes," *J. Immunol.* 155:1296-1303 (1995).
Chen et al., "Selection and Analysis of an Optimized Anti-VEGF Antibody: Crystal Structure of an Affinity-matured Fab in Complex with Antigen," *J. Mol. Biol.* 293:865-881 (1999).

(Continued)

*Primary Examiner* — Meera Natarajan
(74) *Attorney, Agent, or Firm* — Finnegan, Henderson, Farabow, Garrett & Dunner, LLP

(57) ABSTRACT

This invention provides antibodies that recognize the B Cell Maturation Antigen (BCMA) and that bind naïve B cells, plasma cells, and/or memory B cells. The invention further provides methods for depleting naïve B cells, plasma cells, and memory B cells, and for treating B cell-related disorders, including lymphomas and autoimmune diseases.

18 Claims, 16 Drawing Sheets

Specification includes a Sequence Listing.

(56) References Cited

OTHER PUBLICATIONS

Chiu et al., "Hodgkin lymphoma cells express TACI and BCMA receptors and generate survival and proliferation signals in response to BAFF and APRIL," *Blood* 109:729-739 (2007).
Clark et al., "How does B cell depletion therapy work, and how can it be improved?" *Ann. Rheum. Dis.* 64:iv77-iv80 (2005).
Colsky et al., "FcR-Independent Antibody-Mediated Cellular Cytotoxicity," *J. Leukocyte Biol.* 49:548-555 (1991).
Coquery et al., "Regulatory Roles of the Tumor Necrosis Factor Receptor BCMA," *Crit Rev Immunol.* 32(4):287-305 (2012). NIH Public Access Author Manuscript; available in PMC Jan. 18, 2013 (19 pages).
Coquery et al., "T follicular helper cells contribute to autoimmunity through the BCMA-BAFF axis (BA2P.117)," *J. Immunol.* 192(1): Suppl. 45.4 (2014) (Abstract).
Darce et al., "Regulated Expression of BAFF-Binding Receptors during Human B Cell Differentiation," *J. Immunol.* 179:7276-7286 (2007).
Davies and Riechmann, "Affinity improvement of single antibody VH domains: residues in all three hypervariable regions affect antigen binding," *Immunotechnology* 2:169-179 (1996).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," *J. Immunol.* 169:3076-3084 (2002).
Gras et al., "BCMAp: an integral membrane protein in the Golgi apparatus of human mature B lymphocytes," *Int'l. Immunol.* 7(7):1093-1106 (1995).
Harlow and Lane, *Using Antibodies: A Laboratory Manual: Portable Protocol No. I*, Cold Spring Harbor Laboratory, Cold Spring Harbor, NY. (1998).
Hatzoglou et al., "TNF Receptor Family Member BCMA (B Cell Maturation) Associates with TNF Receptor-Associated Factor (TRAF) 1, TRAF2, and TRAF3 and Activates NF-κB, Elk-1, c-Jun N-Terminal Kinase, and p38 Mitogen-Activated Protein Kinase," *J. Immunol.* 165:1322-1330 (2000).
He et al., "Lymphoma B Cells Evade Apoptosis through the TNF Family Members BAFF/BLyS and APRIL," *J. Immunol.* 172:3268-3279 (2004).
Holt et al., "Domain antibodies: proteins for therapy," *Trends in Biotech.* 21(11) 484-490 (2003).
Huang et al., "Homeostatic cell-cycle control by BLyS: Induction of cell-cycle entry but not G1/S transition in opposition to p18INK4c and p27Kip1," *Proc. Natl. Acad. Sci. USA* 101(51):17789-17794 (2004).
Huse et al., "Generation of a Large Combinatorial Library of the Immunoglobulin Repertoire in Phage Lambda," *Science* 246:1275-1281 (1989).
Irani et al., "Production of scFv antibody Fragments from a Hybridoma with Functional Activity Against Human Vascular Endothelial Growth Factor," *Hybridoma* 28(3):205-209 (2009).
Johnson and Wu, "Kabat Database and its applications: 30 years after the first variability plot," *Nucleic Acids Res.* 28(1):214-218 (2000).
Ju et al., "Correlation of expression levels of BLyS and its receptors with multiple myeloma," *Clinical Biochemistry* 42:387-399 (2009).
Kalled et al., "BAFF: B cell survival factor and emerging therapeutic target for autoimmune disorders," *Expert Opin. Ther. Targets* 7(1):115-123 (2003).
Kalled et al., "The Biochemistry and Biology of BAFF, APRIL and Their Receptors," *Curr. Dir. Autoimmun.* 8:206-242 (2005).
Lamminmäki et al., "Crystal Structure of a Recombinant Anti-estradiol Fab Fragment in Complex with 17 ß-Estradiol," *J. Biol. Chem.* 276(39):36687-36694 (2001).

Lantto et al., "Functional Consequences of Insertions and Deletions in the Complementarity-determining Regions of Human Antibodies," *J. Biol. Chem.* 277(47):45108-45114 (2002).
Litinskiy et al., "DCs induce CD40-independent immunoglobulin class switching through BLyS and APRIL," *Nat. Immunol.* 3(9):822-829 (2002).
Liu et al., "Chimeric mouse-human IgG1 antibody that can mediate lysis of cancer cells," *Proc. Natl. Acad. Sci. USA* 84:3439-3443 (1987).
MacCallum. et al., "Antibody-antigen Interactions: Contact Analysis and Binding Site Topography," *J. Mol. Biol.* 262:732-745 (1996).
NCBI GenBank Accession No. XP_523298, "Predicted: tumor necrosis factor receptor superfamily member 17 [Pan troglodytes]," Replaced gi:55643463 on Sep. 15, 2006 (2 pages).
Novak et al., "Expression of BCMA, TACI, and BAFF-R in multiple myeloma: a mechanism for growth and survival," *Blood* 103:689-694 (2004).
Novak et al., "Expression of BLyS and its receptors in B-cell non-Hodgkin lymphoma: correlation with disease activity and patient outcome," *Blood* 104(8):2247-2253 (2004).
O'Connor et al., "BCMA Is Essential for the Survival of Long-lived Bone Marrow Plasma Cells," *J. Exp. Med.* 199(1):91-97 (2004).
Padlan et al., "Structure of an antibody-antigen complex: Crystal structure of the HyHEL-10 Fab—lysozyme complex," *Proc. Natl. Acad. Sci. USA* 86:5938-5942 (1989).
Pearson et al. "Creation of 'Humanized' Mice to Study Human Immunity," *Curr. Protocols in Immunology* 15.21.1-15.21.21 (2008).
Pomerantz and Baltimore, "Two Pathways to NF-κB," *Mol. Cell* 10:693-695 (2002).
Reff et al., "Depletion of B Cells In Vivo by a Chimeric Mouse Human Monoclonal Antibody to CD20," *Blood*, 83(2): 435-445 (1994).
Rudikoff et al., "Single amino acid substitution altering antigen-binding specificity," *Proc. Natl. Acad. Sci. USA* 79:1979-1983 (1982).
Ryan, "Antibody targeting of B-cell maturation antigen on malignant plasma cells," *Mol. Cancer Ther.* 6(11) 3009-3018 (2007).
Schiemann et al., "An Essential Role for BAFF in the Normal Development of B Cells Through a BCMA-Independent Pathway," *Science* 293:2111-2114 (2001).
Schiemann et al., "An Essential Role for BAFF in the Normal Development of B Cells Through a BCMA-Independent Pathway," *Science Express* 10.1126/science.1061964 (2001).
Shivakumar and Ansel, "Targeting B-Lymphocyte Stimulator / B-Cell Activating Factor and a Proliferation-Inducing Ligand in Hematologic Malignancies," *Clin. Lymphoma & Myeloma* 7(2):106-108 (2006).
Sims et al., "Identification and characterization of circulating human transitional B cells," *Blood* 105(11):4390-4398 (2005).
Spira et al., "Generation of Mutant Monoclonal Antibodies," in *Methods of Hybridoma Formation*. A.H. Bartal et al. (eds.) The Humana Press Inc., 1987; pp. 379-397.
Spirodon et al., "A Comparison of the in Vitro and in Vivo Activities of IgG and F(ab')$_2$ Fragments of a Mixture of Three Monoclonal Anti-Her-2 Antibodies," *Clin. Cancer Res.* 10:3542-3551 (2004).
Vajdos et al., "Comprehensive Functional Maps of the Antigen-binding Site of an Anti-ErbB2 Antibody Obtained with Shotgun Scanning Mutagenesis," *J. Mol. Biol.* 320:415-428 (2002).
White et al., "Antibody-Targeted Immunotherapy for Treatment of Malignancy," *Annu. Rev.* 52:125-145 (2001).
Wu et al., "Humanization of a Murine Monoclonal Antibody by Simultaneous Optimization of Framework and CDR Residues," *J. Mol. Biol.* 294:151-162 (1999).
Xu and Lam, "B-Cell Maturation Protein, Which Binds the Tumor Necrosis Factor Family Members BAFF and APRIL, Is Dispensable for Humoral Immune Responses," *Mol. Cell Biol.* 21(12):4067-4074 (2001).
Zhang et al., "BAFF supports human B cell differentiation in the Lymphoid follicles through distinct receptors," *Int'l. Immunol.* 17:779-788 (2005).

```
SEQUENCE LISTING

<160> NUMBER OF SEQ ID NOS: 47

<210> SEQ ID NO 1
<211> LENGTH: 122
<212> TYPE: PRT
<213> ORGANISM: Mus musculus

<400> SEQUENCE: 1

Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr Asn Phe
            20                  25                  30

Gly Met Asn Trp Val Lys Gln Ala Pro Gly Lys Gly Phe Lys Trp Met
        35                  40                  45

Ala Trp Ile Asn Thr Tyr Thr Gly Glu Ser Tyr Phe Ala Asp Asp Phe
    50                  55                  60

Lys Gly Arg Phe Ala Phe Ser Val Glu Thr Ser Ala Thr Thr Ala Tyr
65                  70                  75                  80

Leu Gln Ile Asn Asn Leu Lys Thr Glu Asp Thr Ala Thr Tyr Phe Cys
                85                  90                  95

Ala Arg Gly Glu Ile Tyr Tyr Gly Tyr Asp Gly Gly Phe Ala Tyr Trp
            100                 105                 110

Gly Gln Gly Thr Leu Val Thr Val Ser Ala
        115                 120

<210> SEQ ID NO 2
<211> LENGTH: 107
<212> TYPE: PRT
<213> ORGANISM: Mus musculus

<400> SEQUENCE: 2

Asp Val Val Met Thr Gln Ser His Arg Phe Met Ser Thr Ser Val Gly
1               5                   10                  15

Asp Arg Val Ser Ile Thr Cys Arg Ala Ser Gln Asp Val Asn Thr Ala
            20                  25                  30

Val Ser Trp Tyr Gln Gln Lys Pro Gly Gln Ser Pro Lys Leu Leu Ile
        35                  40                  45
```

Phe Ser Ala Ser Tyr Arg Tyr Thr Gly Val Pro Asp Arg Phe Thr Gly
            50                  55                  60

Ser Gly Ser Gly Ala Asp Phe Thr Leu Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Asp Ile Lys
            100                 105

<210> SEQ ID NO 3
<211> LENGTH: 117
<212> TYPE: PRT
<213> ORGANISM: Mus musculus

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115

<210> SEQ ID NO 4
<211> LENGTH: 111
<212> TYPE: PRT
<213> ORGANISM: Mus musculus

<400> SEQUENCE: 4

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 5
<211> LENGTH: 117
<212> TYPE: PRT
<213> ORGANISM: Mus musculus

<400> SEQUENCE: 5

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg His Tyr
            20                  25                  30

Ser Met Asn Trp Val Lys Gln Ala Pro Gly Lys Gly Leu Lys Trp Met
        35                  40                  45

Gly Arg Ile Asn Thr Glu Ser Gly Val Pro Ile Tyr Ala Asp Asp Phe
50                  55                  60

Lys Gly Arg Phe Ala Phe Ser Val Glu Thr Ser Ala Ser Thr Ala Tyr
65                  70                  75                  80

Leu Val Ile Asn Asn Leu Lys Asp Glu Asp Thr Ala Ser Tyr Phe Cys
            85                  90                  95

Ser Asn Asp Tyr Leu Tyr Ser Leu Asp Phe Trp Gly Gln Gly Thr Ala
            100                 105                 110

Leu Thr Val Ser Ser
        115

<210> SEQ ID NO 6
<211> LENGTH: 111
<212> TYPE: PRT
<213> ORGANISM: Mus musculus

<400> SEQUENCE: 6

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 7
<211> LENGTH: 117
<212> TYPE: PRT
<213> ORGANISM: Mus musculus

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Ser Met Asn Trp Val Lys Gln Ala Pro Gly Lys Gly Leu Lys Trp Met
        35                  40                  45

Gly Arg Ile Asn Thr Glu Thr Gly Glu Pro Leu Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Val Ile Asn Asn Leu Lys Asn Glu Asp Thr Ala Thr Phe Phe Cys
                    85                  90                  95

Ser Asn Asp Tyr Leu Tyr Ser Cys Asp Tyr Trp Gly Gln Gly Thr Thr
            100                 105                 110

Leu Thr Val Ser Ser
        115

<210> SEQ ID NO 8
<211> LENGTH: 111
<212> TYPE: PRT
<213> ORGANISM: Mus musculus

<400> SEQUENCE: 8

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 9
<211> LENGTH: 184
<212> TYPE: PRT
<213> ORGANISM: Homo sapiens

<400> SEQUENCE: 9

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 10
<211> LENGTH: 282
<212> TYPE: PRT
<213> ORGANISM: Homo sapiens

<400> SEQUENCE: 10

Asp Val Thr Met Leu Gln Met Ala Gly Gln Cys Ser Gln Asn Glu Tyr
1               5                   10                  15

Phe Asp Ser Leu Leu His Ala Cys Ile Pro Cys Gln Leu Arg Cys Ser
            20                  25                  30

Ser Asn Thr Pro Pro Leu Thr Cys Gln Arg Tyr Cys Asn Ala Ser Val
        35                  40                  45

Thr Asn Ser Val Lys Gly Val Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 11
<211> LENGTH: 111
<212> TYPE: PRT
<213> ORGANISM: Mus musculus

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Phe Ser Phe Met His Trp Tyr Gln Gln Lys Pro Gly Gln Pro Pro
                35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Ala Leu Thr Ile Asn
 65                  70                  75                  80

Pro Val Glu Thr Asp Asp Val Ala Thr Tyr Tyr Cys Gln Gln Ser Asn
                 85                  90                  95

Lys Asp Pro Arg Thr Phe Gly Gly Gly Thr Lys Leu Glu Ile Lys
                100                 105                 110

<210> SEQ ID NO 12
<211> LENGTH: 111
<212> TYPE: PRT
<213> ORGANISM: Mus sp.

<400> SEQUENCE: 12

Asp Ile Val Leu Thr Gln Ser Pro Ala Ser Leu Ala Met Ser Leu Gly
 1               5                  10                  15

Lys Arg Ala Thr Ile Ser Cys Arg Ala Ser Glu Ser Val Ser Val Ile
                20                  25                  30

Gly Ala His Leu Ile His Trp Tyr Gln Gln Lys Pro Gly Gln Pro Pro
                35                  40                  45

Lys Leu Leu Ile Tyr Leu Ala Ser Asn Leu Glu Thr Gly Val Pro Ala
 50                  55                  60

Arg Phe Ser Gly Ser Gly Ser Gly Thr Asp Phe Thr Leu Thr Ile Asp
 65                  70                  75                  80

Pro Val Glu Glu Asp Asp Val Ala Ile Tyr Ser Cys Leu Gln Ser Arg
                 85                  90                  95

Ile Phe Pro Arg Thr Phe Gly Gly Gly Thr Lys Leu Glu Ile Lys
                100                 105                 110

<210> SEQ ID NO 13
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Ile Gln Leu Val Gln Ser Gly Pro Asp Leu Lys Lys Pro Gly Glu
 1               5                  10                  15

Thr Val Lys Leu Ser Cys Lys Ala Ser Gly Tyr Thr Phe Thr Asn Phe
                20                  25                  30

Gly Met Asn Trp Val Lys Gln Ala Pro Gly Lys Gly Phe Lys Trp Met
                35                  40                  45

Ala Trp Ile Asn Thr Tyr Thr Gly Glu Ser Tyr Phe Ala Asp Asp Phe
 50                  55                  60

Lys Gly Arg Phe Ala Phe Ser Val Glu Thr Ser Ala Thr Thr Ala Tyr
 65                  70                  75                  80

Leu Gln Ile Asn Asn Leu Lys Thr Glu Asp Thr Ala Thr Tyr Phe Cys
                 85                  90                  95

Ala Arg Gly Glu Ile Tyr Tyr Gly Tyr Asp Gly Gly Phe Ala Tyr Trp
                100                 105                 110

Gly Gln Gly Thr Leu Val Thr Val Ser Ala Ala Ser Thr Lys Gly Pro
                115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 14
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asp Val Val Met Thr Gln Ser His Arg Phe Met Ser Thr Ser Val Gly
1               5                   10                  15

```
Asp Arg Val Ser Ile Thr Cys Arg Ala Ser Gln Asp Val Asn Thr Ala
                20                  25                  30

Val Ser Trp Tyr Gln Gln Lys Pro Gly Gln Ser Pro Lys Leu Leu Ile
            35                  40                  45

Phe Ser Ala Ser Tyr Arg Tyr Thr Gly Val Pro Asp Arg Phe Thr Gly
        50                  55                  60

Ser Gly Ser Gly Ala Asp Phe Thr Leu Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Ile Asn Trp Val Lys Arg Ala Pro Gly Lys Gly Leu Lys Trp Met
            35                  40                  45

Gly Trp Ile Asn Thr Glu Thr Arg Glu Pro Ala Tyr Ala Tyr Asp Phe
        50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
```

```
                145                 150                 155                 160
        Gly Ala Leu Thr Ser Gly Val His Thr Phe Pro Ala Val Leu Gln Ser
                        165                 170                 175

Ser Gly Leu Tyr Ser Leu Ser Ser Val Val Thr Val Pro Ser Ser Ser
                        180                 185                 190

Leu Gly Thr Gln Thr Tyr Ile Cys Asn Val Asn His Lys Pro Ser Asn
                        195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
        225                 230                 235                 240

Phe Leu Phe Pro Pro Lys Pro Lys Asp Thr Leu Met Ile Ser Arg Thr
                        245                 250                 255

Pro Glu Val Thr Cys Val Val Val Asp Val Ser His Glu Asp Pro Glu
                        260                 265                 270

Val Lys Phe Asn Trp Tyr Val Asp Gly Val Glu Val His Asn Ala Lys
                        275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
        305                 310                 315                 320

Cys Lys Val Ser Asn Lys Ala Leu Pro Ala Pro Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Arg Asp Glu Leu Thr Lys Asn Gln Val Ser Leu Thr Cys Leu
                        355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Lys Leu Thr Val Asp Lys Ser Arg
                        405                 410                 415

Trp Gln Gln Gly Asn Val Phe Ser Cys Ser Val Met His Glu Ala Leu
                        420                 425                 430

His Asn His Tyr Thr Gln Lys Ser Leu Ser Leu Ser Pro Gly
                        435                 440                 445

<210> SEQ ID NO 16
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
                20                  25                  30

Gly Ser His Leu Ile His Trp Tyr Gln Gln Lys Pro Gly Gln Pro Pro
            35                  40                  45

Thr Leu Leu Ile Gln Leu Ala Ser Asn Val Gln Thr Gly Val Pro Ala
        50                  55                  60
```

```
Arg Phe Ser Gly Ser Gly Ser Arg Thr Asp Phe Thr Leu Thr Ile Asp
 65                  70                  75                  80

Pro Val Glu Glu Asp Val Ala Val Tyr Tyr Cys Leu Gln Ser Arg
                 85                  90                  95

Thr Ile Pro Arg Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 17
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Asp Ile Val Leu Thr Gln Ser Pro Ala Ser Leu Ala Met Ser Leu Gly
 1               5                  10                  15

Lys Arg Ala Thr Ile Ser Cys Arg Ala Ser Glu Ser Val Ser Val Ile
             20                  25                  30

Gly Ala His Leu Ile His Trp Tyr Gln Gln Lys Pro Gly Gln Pro Pro
         35                  40                  45

Lys Leu Leu Ile Tyr Leu Ala Ser Asn Leu Glu Thr Gly Val Pro Ala
 50                  55                  60

Arg Phe Ser Gly Ser Gly Ser Gly Thr Asp Phe Thr Leu Thr Ile Asp
 65                  70                  75                  80

Pro Val Glu Glu Asp Val Ala Ile Tyr Ser Cys Leu Gln Ser Arg
                 85                  90                  95

Ile Phe Pro Arg Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 18
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg His Tyr
            20                  25                  30

Ser Met Asn Trp Val Lys Gln Ala Pro Gly Lys Gly Leu Lys Trp Met
        35                  40                  45

Gly Arg Ile Asn Thr Glu Ser Gly Val Pro Ile Tyr Ala Asp Asp Phe
    50                  55                  60

Lys Gly Arg Phe Ala Phe Ser Val Glu Thr Ser Ala Ser Thr Ala Tyr
65                  70                  75                  80

Leu Val Ile Asn Asn Leu Lys Asp Glu Asp Thr Ala Ser Tyr Phe Cys
                85                  90                  95

Ser Asn Asp Tyr Leu Tyr Ser Leu Asp Phe Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile

```
              325                 330                 335
Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 19
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 20
```

```
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Ser Met Asn Trp Val Lys Gln Ala Pro Gly Lys Gly Leu Lys Trp Met
        35                  40                  45

Gly Arg Ile Asn Thr Glu Thr Gly Glu Pro Leu Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Val Ile Asn Asn Leu Lys Asn Glu Asp Thr Ala Thr Phe Phe Cys
                85                  90                  95

Ser Asn Asp Tyr Leu Tyr Ser Cys Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 21
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Pro Pro
        35                  40                  45

Thr Leu Leu Ile Gln Leu Ala Ser Asn Val Gln Thr Gly Val Pro Ala
50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 22
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys
            100                 105                 110

<210> SEQ ID NO 23
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Ser Cys Leu Gln Ser Arg
                85                  90                  95

Ile Phe Pro Arg Thr Phe Gly Gln Gly Thr Lys Leu Glu Ile Lys
            100                 105                 110

<210> SEQ ID NO 24
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

Asp Ile Val Leu Thr Gln Ser Pro Ala Ser Leu Ala Met Ser Leu Gly
1               5                   10                  15

Glu Arg Ala Thr Ile Ser Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Arg Val Gln Ala Glu Asp Ala Ala Ile Tyr Ser Cys Leu Gln Ser Arg
                85                  90                  95

Ile Phe Pro Arg Thr Phe Gly Gly Thr Lys Leu Glu Ile Lys
            100                 105                 110

<210> SEQ ID NO 25
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 25

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ser Ile Asn Trp Val Arg Gln Ala Pro Gly Gln Gly Leu Glu Trp Met
            35                  40                  45

Gly Trp Ile Asn Thr Glu Thr Arg Glu Pro Ala Tyr Ala Tyr Asp Phe
        50                  55                  60

Arg Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Ser Tyr Ala Met Asp Tyr Trp Gly Gln Gly Thr Leu
            100                 105                 110

Val Thr Val Ser Ser
        115

<210> SEQ ID NO 26
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 26

Gln Val Gln Leu Val Gln Ser Gly Ser Glu Leu Lys Lys Pro Gly Glu
1               5                   10                  15

Ser Val Lys Val Ser Cys Lys Ala Ser Gly Tyr Thr Phe Thr Asp Tyr
                20                  25                  30

Ser Ile Asn Trp Val Arg Gln Ala Pro Gly Gln Gly Leu Glu Trp Met
            35                  40                  45

Gly Trp Ile Asn Thr Glu Thr Arg Glu Pro Ala Tyr Ala Tyr Asp Phe
        50                  55                  60

Arg Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Leu Asp Tyr Ser Tyr Ala Met Asp Tyr Trp Gly Gln Gly Thr Leu
            100                 105                 110

Val Thr Val Ser Ser
        115

<210> SEQ ID NO 27
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr Asp Tyr
                20                  25                  30

Ser Ile Asn Trp Val Arg Gln Ala Pro Gly Gln Gly Leu Glu Trp Met
            35                  40                  45

Gly Trp Ile Asn Thr Glu Thr Arg Glu Pro Ala Tyr Ala Tyr Asp Phe
        50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Leu Asp Tyr Ser Tyr Ala Met Asp Tyr Trp Gly Gln Gly Thr Leu
                100                 105                 110

Val Thr Val Ser Ser
        115

<210> SEQ ID NO 28
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gln Val Gln Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr Asp Tyr
                20                  25                  30

Ser Ile Asn Trp Val Lys Gln Ala Pro Gly Gln Gly Leu Lys Trp Met
            35                  40                  45

Gly Trp Ile Asn Thr Glu Thr Arg Glu Pro Ala Tyr Ala Tyr Asp Phe
        50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Leu Asp Tyr Ser Tyr Ala Met Asp Tyr Trp Gly Gln Gly Thr Leu
                100                 105                 110

Val Thr Val Ser Ser
        115

<210> SEQ ID NO 29
<211> LENGTH: 117
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Ile Gln Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ser Ile Asn Trp Val Lys Gln Ala Pro Gly Gln Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Leu Asp Tyr Ser Tyr Ala Met Asp Tyr Trp Gly Gln Gly Thr Leu
            100                 105                 110

Val Thr Val Ser Ser
        115

<210> SEQ ID NO 30
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Ile Val Leu Thr Gln Ser Pro Ala Thr Leu Ser Leu Ser Pro Gly
1               5                   10                  15

Asp Arg Ala Thr Leu Ser Cys Arg Ala Ser Glu Ser Val Thr Ile Leu
            20                  25                  30

Gly Ser His Leu Ile Tyr Trp Tyr Gln Gln Lys Pro Gly Gln Ala Pro
        35                  40                  45

Arg Leu Leu Ile Tyr Leu Ala Ser Asn Val Gln Thr Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Leu Gln Ser Arg
                85                  90                  95

Thr Ile Pro Arg Thr Phe Gly Gln Gly Thr Lys Leu Glu Ile Lys Arg
            100                 105                 110

<210> SEQ ID NO 31
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Ile Val Leu Thr Gln Ser Pro Ala Thr Leu Ser Leu Ser Pro Gly
1               5                   10                  15

```
Asp Arg Ala Thr Leu Ser Cys Arg Ala Ser Glu Ser Val Thr Ile Leu
                20                  25                  30

Gly Ser His Leu Ile Tyr Trp Tyr Gln Gln Lys Pro Gly Gln Ala Pro
            35                  40                  45

Arg Leu Leu Ile Gln Leu Ala Ser Asn Val Gln Thr Gly Ile Pro Ala
 50                  55                  60

Arg Phe Ser Gly Ser Gly Ser Arg Thr Asp Phe Thr Leu Thr Ile Ser
 65                  70                  75                  80

Ser Leu Glu Pro Glu Asp Phe Ala Val Tyr Tyr Cys Leu Gln Ser Arg
                85                  90                  95

Thr Ile Pro Arg Thr Phe Gly Gln Gly Thr Lys Leu Glu Ile Lys Arg
            100                 105                 110

<210> SEQ ID NO 32
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Asp Ile Val Leu Thr Gln Ser Pro Ala Thr Leu Ser Leu Ser Pro Gly
 1               5                  10                  15

Asp Arg Ala Thr Ile Ser Cys Arg Ala Ser Glu Ser Val Thr Ile Leu
                20                  25                  30

Gly Ser His Leu Ile Tyr Trp Tyr Gln Gln Lys Pro Gly Gln Ala Pro
            35                  40                  45

Arg Leu Leu Ile Gln Leu Ala Ser Asn Val Gln Thr Gly Ile Pro Ala
 50                  55                  60

Arg Phe Ser Gly Ser Gly Ser Arg Thr Asp Phe Thr Leu Thr Ile Ser
 65                  70                  75                  80

Ser Val Glu Pro Glu Asp Phe Ala Val Tyr Tyr Cys Leu Gln Ser Arg
                85                  90                  95

Thr Ile Pro Arg Thr Phe Gly Gln Gly Thr Lys Leu Glu Ile Lys Arg
            100                 105                 110

<210> SEQ ID NO 33
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ile Val Leu Thr Gln Ser Pro Ala Thr Leu Ser Leu Ser Pro Gly
 1               5                  10                  15

Asp Arg Ala Thr Ile Ser Cys Arg Ala Ser Glu Ser Val Thr Ile Leu
                20                  25                  30

Gly Ser His Leu Ile Tyr Trp Tyr Gln Gln Lys Pro Gly Gln Pro Pro
            35                  40                  45

Arg Leu Leu Ile Gln Leu Ala Ser Asn Val Gln Thr Gly Val Pro Ala
 50                  55                  60

Arg Phe Ser Gly Ser Gly Ser Arg Thr Asp Phe Thr Leu Thr Ile Ser
 65                  70                  75                  80
```

Ser Val Glu Pro Glu Asp Phe Ala Val Tyr Tyr Cys Leu Gln Ser Arg
            85                  90                  95

Thr Ile Pro Arg Thr Phe Gly Gln Gly Thr Lys Leu Glu Ile Lys Arg
            100                 105                 110

<210> SEQ ID NO 34
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Gln Val Gln Leu Val Gln Ser Gly Pro Glu Val Lys Lys Pro Gly Ser
1               5                   10                  15

Ser Val Lys Val Ser Cys Lys Ala Ser Gly Tyr Thr Phe Arg His Tyr
            20                  25                  30

Ser Met Asn Trp Val Arg Gln Ala Pro Gly Gln Gly Leu Glu Trp Met
        35                  40                  45

Gly Arg Ile Asn Thr Glu Ser Gly Val Pro Ile Tyr Ala Asp Asp Phe
    50                  55                  60

Lys Gly Arg Val Ser Phe Thr Val Asp Glu Ser Thr Ser Thr Ala Tyr
65                  70                  75                  80

Met Glu Leu Ser Ser Leu Thr Ser Glu Asp Thr Ala Val Tyr Tyr Cys
            85                  90                  95

Ala Arg Asp Tyr Leu Tyr Ser Leu Asp Phe Trp Gly Gln Gly Thr Thr
            100                 105                 110

Val Thr Val Ser Ser
        115

<210> SEQ ID NO 35
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Val Gln Leu Val Gln Ser Gly Pro Glu Val Lys Lys Pro Gly Glu
1               5                   10                  15

Ser Val Lys Val Ser Cys Lys Ala Ser Gly Tyr Thr Phe Arg His Tyr
            20                  25                  30

Ser Met Asn Trp Val Arg Gln Ala Pro Gly Gln Gly Leu Glu Trp Met
        35                  40                  45

Gly Arg Ile Asn Thr Glu Ser Gly Val Pro Ile Tyr Ala Asp Asp Phe
    50                  55                  60

Lys Gly Arg Val Ser Phe Thr Val Asp Glu Ser Thr Ser Thr Ala Tyr
65                  70                  75                  80

Met Glu Leu Ser Ser Leu Thr Ser Glu Asp Thr Ala Val Tyr Tyr Cys
            85                  90                  95

Ala Asn Asp Tyr Leu Tyr Ser Leu Asp Phe Trp Gly Gln Gly Thr Thr
            100                 105                 110

Val Thr Val Ser Ser
        115

```
<210> SEQ ID NO 36
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36
```

Gln Val Gln Leu Val Gln Ser Gly Pro Glu Val Lys Lys Pro Gly Glu
1               5                   10                  15

Ser Val Lys Val Ser Cys Lys Ala Ser Gly Tyr Thr Phe Arg His Tyr
            20                  25                  30

Ser Met Asn Trp Val Arg Gln Ala Pro Gly Gln Gly Leu Glu Trp Met
        35                  40                  45

Gly Arg Ile Asn Thr Glu Ser Gly Val Pro Ile Tyr Ala Asp Asp Phe
    50                  55                  60

Lys Gly Arg Phe Ser Phe Thr Val Asp Thr Ser Ala Ser Thr Ala Tyr
65                  70                  75                  80

Met Glu Leu Ser Ser Leu Thr Ser Glu Asp Thr Ala Val Tyr Phe Cys
                85                  90                  95

Ser Asn Asp Tyr Leu Tyr Ser Leu Asp Phe Trp Gly Gln Gly Thr Thr
            100                 105                 110

Val Thr Val Ser Ser
        115

```
<210> SEQ ID NO 37
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37
```

Gln Val Gln Leu Val Gln Ser Gly Pro Glu Val Lys Lys Pro Gly Glu
1               5                   10                  15

Ser Val Lys Ile Ser Cys Lys Ala Ser Gly Tyr Thr Phe Arg His Tyr
            20                  25                  30

Ser Met Asn Trp Val Lys Gln Ala Pro Gly Gln Gly Leu Lys Trp Met
        35                  40                  45

Gly Arg Ile Asn Thr Glu Ser Gly Val Pro Ile Tyr Ala Asp Asp Phe
    50                  55                  60

Lys Gly Arg Phe Ser Phe Thr Val Asp Thr Ser Ala Ser Thr Ala Tyr
65                  70                  75                  80

Leu Glu Ile Ser Ser Leu Thr Ser Glu Asp Thr Ala Val Tyr Phe Cys
                85                  90                  95

Ser Asn Asp Tyr Leu Tyr Ser Leu Asp Phe Trp Gly Gln Gly Thr Thr
            100                 105                 110

Leu Thr Val Ser Ser
        115

```
<210> SEQ ID NO 38
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
```

```
<400> SEQUENCE: 38

Gln Ile Gln Leu Val Gln Ser Gly Pro Glu Val Lys Pro Gly Glu
1               5                   10                  15

Ser Val Lys Ile Ser Cys Lys Ala Ser Gly Tyr Thr Phe Arg His Tyr
                20                  25                  30

Ser Met Asn Trp Val Lys Gln Ala Pro Gly Gln Gly Leu Lys Trp Met
            35                  40                  45

Gly Arg Ile Asn Thr Glu Ser Gly Val Pro Ile Tyr Ala Asp Asp Phe
    50                  55                  60

Lys Gly Arg Phe Ser Phe Thr Val Asp Thr Ser Ala Ser Thr Ala Tyr
65                  70                  75                  80

Leu Glu Ile Ser Ser Leu Thr Ser Glu Asp Thr Ala Val Tyr Phe Cys
                85                  90                  95

Ser Asn Asp Tyr Leu Tyr Ser Leu Asp Phe Trp Gly Gln Gly Thr Thr
                100                 105                 110

Leu Thr Val Ser Ser
            115

<210> SEQ ID NO 39
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Glu Ile Val Leu Thr Gln Ser Pro Ala Thr Leu Ser Leu Ser Pro Gly
1               5                   10                  15

Asp Arg Ala Thr Leu Ser Cys Arg Ala Ser Glu Ser Val Thr Ile Leu
                20                  25                  30

Gly Ser His Leu Ile Tyr Trp Tyr Gln Gln Lys Pro Gly Gln Ala Pro
            35                  40                  45

Arg Leu Leu Ile Tyr Leu Ala Ser Asn Val Gln Thr Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Leu Gln Ser Arg
                85                  90                  95

Thr Ile Pro Arg Thr Phe Gly Gln Gly Thr Lys Leu Glu Ile Lys Arg
                100                 105                 110

<210> SEQ ID NO 40
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Ile Val Leu Thr Gln Ser Pro Ala Thr Leu Ser Leu Ser Pro Gly
1               5                   10                  15

Asp Arg Ala Thr Leu Ser Cys Arg Ala Ser Glu Ser Val Thr Ile Leu
                20                  25                  30
```

Gly Ser His Leu Ile Tyr Trp Tyr Gln Gln Lys Pro Gly Gln Ala Pro
            35                  40                  45

Arg Leu Leu Ile Gln Leu Ala Ser Asn Val Gln Thr Gly Ile Pro Ala
 50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Leu Gln Ser Arg
                85                  90                  95

Thr Ile Pro Arg Thr Phe Gly Gln Gly Thr Lys Leu Glu Ile Lys Arg
            100                 105                 110

<210> SEQ ID NO 41
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Asp Ile Val Leu Thr Gln Ser Pro Ala Thr Leu Ser Leu Ser Pro Gly
1               5                   10                  15

Asp Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Ala Pro
            35                  40                  45

Arg Leu Leu Ile Gln Leu Ala Ser Asn Val Gln Thr Gly Ile Pro Ala
 50                  55                  60

Arg Phe Ser Gly Ser Gly Ser Arg Thr Asp Phe Thr Leu Thr Ile Ser
65                  70                  75                  80

Ser Val Glu Pro Glu Asp Phe Ala Val Tyr Tyr Cys Leu Gln Ser Arg
                85                  90                  95

Thr Ile Pro Arg Thr Phe Gly Gln Gly Thr Lys Leu Glu Ile Lys Arg
            100                 105                 110

<210> SEQ ID NO 42
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Asp Ile Val Leu Thr Gln Ser Pro Ala Thr Leu Ser Leu Ser Pro Gly
1               5                   10                  15

Asp Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Pro Pro
            35                  40                  45

Arg Leu Leu Ile Gln Leu Ala Ser Asn Val Gln Thr Gly Val Pro Ala
 50                  55                  60

Arg Phe Ser Gly Ser Gly Ser Arg Thr Asp Phe Thr Leu Thr Ile Ser
65                  70                  75                  80

Ser Val Glu Pro Glu Asp Phe Ala Val Tyr Tyr Cys Leu Gln Ser Arg
                85                  90                  95

Thr Ile Pro Arg Thr Phe Gly Gln Gly Thr Lys Leu Glu Ile Lys Arg

<210> SEQ ID NO 43
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr His Tyr
                20                  25                  30
Ser Met Asn Trp Val Arg Gln Ala Pro Gly Gln Gly Leu Glu Trp Met
            35                  40                  45
Gly Arg Ile Asn Thr Glu Thr Gly Glu Pro Leu Tyr Ala Asp Asp Phe
        50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Asp Tyr Leu Tyr Ser Leu Asp Tyr Trp Gly Gln Gly Thr Leu
            100                 105                 110
Val Thr Val Ser Ser
        115

<210> SEQ ID NO 44
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

Gln Val Gln Leu Val Gln Ser Gly Ser Glu Leu Lys Lys Pro Gly Glu
1               5                   10                  15
Ser Val Lys Val Ser Cys Lys Ala Ser Gly Tyr Thr Phe Thr His Tyr
                20                  25                  30
Ser Met Asn Trp Val Arg Gln Ala Pro Gly Gln Gly Leu Glu Trp Met
            35                  40                  45
Gly Arg Ile Asn Thr Glu Thr Gly Glu Pro Leu Tyr Ala Asp Asp Phe
        50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Asn Asp Tyr Leu Tyr Ser Leu Asp Tyr Trp Gly Gln Gly Thr Leu
            100                 105                 110
Val Thr Val Ser Ser
        115

<210> SEQ ID NO 45
<211> LENGTH: 117
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 45

Gln Val Gln Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr His Tyr
            20                  25                  30

Ser Met Asn Trp Val Arg Gln Ala Pro Gly Gln Gly Leu Glu Trp Met
        35                  40                  45

Gly Arg Ile Asn Thr Glu Thr Gly Glu Pro Leu Tyr Ala Asp Asp Phe
    50                  55                  60

Lys Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ser Asn Asp Tyr Leu Tyr Ser Leu Asp Tyr Trp Gly Gln Gly Thr Leu
            100                 105                 110

Val Thr Val Ser Ser
        115

<210> SEQ ID NO 46
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Val Gln Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr His Tyr
            20                  25                  30

Ser Met Asn Trp Val Arg Gln Ala Pro Gly Gln Gly Leu Glu Trp Met
        35                  40                  45

Gly Arg Ile Asn Thr Glu Thr Gly Glu Pro Leu Tyr Ala Asp Lys Phe
    50                  55                  60

Lys Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ser Asn Asp Tyr Leu Tyr Ser Leu Asp Tyr Trp Gly Gln Gly Thr Leu
            100                 105                 110

Leu Thr Val Ser Ser
        115

<210> SEQ ID NO 47
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47
```

```
Gln Ile Gln Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr His Tyr
            20                  25                  30

Ser Met Asn Trp Val Arg Gln Ala Pro Gly Gln Gly Leu Glu Trp Met
        35                  40                  45

Gly Arg Ile Asn Thr Glu Thr Gly Glu Pro Leu Tyr Ala Asp Lys Phe
    50                  55                  60

Lys Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ser Asn Asp Tyr Leu Tyr Ser Leu Asp Tyr Trp Gly Gln Gly Thr Leu
            100                 105                 110

Leu Thr Val Ser Ser
            115
```

ANTI-BCMA ANTIBODIES

CROSS-REFERENCE TO RELATED APPLICATIONS

This application is a continuation of U.S. patent application Ser. No. 15/065,641, filed Mar. 9, 2016, which is a continuation of U.S. patent application Ser. No. 14/596,769, filed Jan. 14, 2015, which is a continuation of U.S. patent application Ser. No. 13/255,610, filed Nov. 23, 2011, now U.S. Pat. No. 9,034,324, which issued May 19, 2015, which is a National Stage Entry of PCT/US2010/026825, filed Mar. 10, 2010, which claims the benefit of U.S. Provisional Application No. 61/162,924, filed Mar. 24, 2009, and U.S. Provisional Application No. 61/158,942, filed Mar. 10, 2009. All of these applications are incorporated herein by reference in their entirety.

REFERENCE TO SEQUENCE LISTING

The instant application contains a Sequence Listing which has been submitted via EFS-Web and is hereby incorporated by reference in its entirety. The ASCII copy, created on Mar. 10, 2010, is named 08201010.txt, and is 70,657 bytes in size.

BACKGROUND

This invention relates to antibodies that bind to the B cell surface antigen BCMA. The invention also relates to the use of these antibodies to detect, deplete, and otherwise manipulate various B cell subtypes.

B cells are lymphocytes that play major roles in adaptive humoral immunity and production of antibodies that specifically recognize antigens. Three subclasses of B cells are naïve B cells, memory B cells, and plasma cells. The processes of VDJ recombination, in which two or three segments of DNA are chosen from a genomic library and recombined to generate a combinatorial array of antibody variable domains, and hypermutation, by which the variable domains encoded by different lineages of B cells are further varied, result in up to $10^9$ distinct B cell lineages that produce antibodies with specificity for distinct targets. A B cell is said to be specific for an antigen that binds the antibodies made by that B cell. B cells in general are stimulated by exposure to their specific antigen (Ag). Naïve B cells have not yet been exposed to their specific antigen. Such exposure (e.g., during an infection) results in proliferation of B cells and generation of sister clones. Sister clones can develop into plasma cells, which produce high amounts of antibody. Plasma cells may either be short lived, or may migrate into bone marrow, where they can persist for an extended period of time. A sister clone of an Ag-exposed B cell may also develop into a memory B cell that is quiescent until reexposed to the specific antigen. Memory B cells respond rapidly to reexposure to antigen by dividing to produce both plasma cells and additional memory B cells. Memory B cells include switched memory B cells ($CD19^+ CD27^{high} CD38^{low}$ $IgD^-$), unswitched memory B cells ($CD19^+ CD27^{high} CD38^{low}$ $IgD^+$), and double negative memory B cells ($CD19^+ CD27^- CD38^{low}$ $IgD^-$).

Several significant diseases involve B cells. Malignant transformation of B cells leads to cancers, including some lymphomas such as, for example, multiple myeloma and Hodgkins' Lymphoma. Some autoimmune diseases, including systemic lupus erythematosus (SLE), also involve B cells. Both cancer and autoimmune diseases that involve B cells may be considered gain of function conditions, in that the B cells overgrow and/or attack parts of the body inappropriately. A possible strategy to control such diseases is to use antibodies that target the pathological B cells.

The B cell maturation antigen (BCMA, also known as TNFRSF17 and CD269) is a protein that has been shown to be expressed on the surface of plasmablasts (i.e., plasma cell precursors) and plasma cells, and is believed to stimulate survival. It therefore represents a potential target for B cell-related diseases. BCMA is a member of the TNF receptor family and binds the TNF family ligands BAFF and APRIL (reviewed in Kalled et al. (2005), *Curr Dir Autoimmun* 8:206-242). BCMA is a type III membrane protein, as it lacks the signal peptide associated with type I membrane proteins found in most TNF receptor family members.

BCMA RNA has been detected in the spleen, lymph nodes, thymus, adrenals and liver, and analysis of a number of B cell lines indicated that BCMA mRNA levels increased upon maturation. Human BCMA protein has been detected on various subtypes of $CD38^+$ B cells, particularly plasma cells (Zhang et al. (2005), *Int Immunol* 17:779-788; Darce et al. (2007), *J Immunol* 179:7276-7286; Sims et al. (2005), *Blood* 105:4390-4398; Avery et al. (2003), *J Clin Invest* 112:286-297). Independent laboratories have examined blood and/or tonsil B cell subsets and found that BCMA expression could not be detected on naïve or memory B cells (Zhang et al. (2005), *Int Immunol* 17:779-788; Darce et al. (2007), *J Immunol* 179:7276-7286; Chiu et al. (2007), *Blood* 109:729-739). Attempts to detect BCMA protein on the surface of germinal center B cells have had inconsistent results (Zhang et al. (2005), *Int Immunol* 17:779-788; Chiu et al. (2007), *Blood* 109:729-739).

The mechanism of action of BCMA is not fully understood. Mice that have been genetically altered to lack a functional gene for BCMA have normal lymphoid organs and cell populations, and a nearly normal functioning immune system (Xu and Lam (2001), *Mol Cell Biol* 21:4067-4074; Schiemann et al. (2001), *Science* 293:2111-2114). The only defect defined to date in these mice is a diminished survival of long-lived bone marrow (BM) plasma cells (O'Connor et al. (2004), *J Exp Med* 199:91-98). Therefore, it may be that BCMA, at least in the murine system, provides a survival signal to BM-resident plasma cells that is either BAFF or APRIL-mediated, or both. Indeed, signalling through BCMA activates the NF-κB pathway (Hatzoglou et al. (2000), *J Immunol* 165:1322-1330) which is involved in B cell survival, proliferation and maturation (Litinskiy et al. (2002) *Nat Immunol* 3:822-829; Pomerantz and Baltimore (2002) *Mol Cell* 10:693-695; Huang et al. (2004) *Proc Natl Acad Sci USA* 101:17789-17794; He et al. (2004) *J Immunol* 172:3268-3279). Results with malignant human cells are generally consistent with a link between BCMA and cell survival. Primary multiple myeloma (MM) cells, MM cell lines (Novak et al. (2004) *Blood* 103:689-694), and Hodgkin and Reed-Sternberg (HRS) cells from Hodgkin lymphomas (Chiu et al. (2007), *Blood* 109:729-739; Novak et al. (2004), *Blood* 104:2247-2253) have been shown to express BCMA. Addition of BAFF and/or APRIL has further been shown to provide a survival signal for these malignant cells, although it is not clear that BCMA is predominantly responsible for this effect.

Because different B cell subsets are implicated in different B cell related conditions, there exists a need for agents that specifically target one or more B cell subsets. The expression of BCMA on the surface of some B cells provides a marker by which those cells may be specifically targeted. To take advantage of BCMA as a marker of one or more B cell subsets, there is a need for agents that specifically bind to BCMA and for a determination of which B cell subsets are bound by those BCMA-specific agents. The invention provides antibodies that specifically bind to BCMA. The antibodies of the invention may be used to target one or more of the following B cell subsets: plasma cells, memory B cells, and naïve B cells.

TABLE 1

Brief Description of the Sequences

Figure 1A:
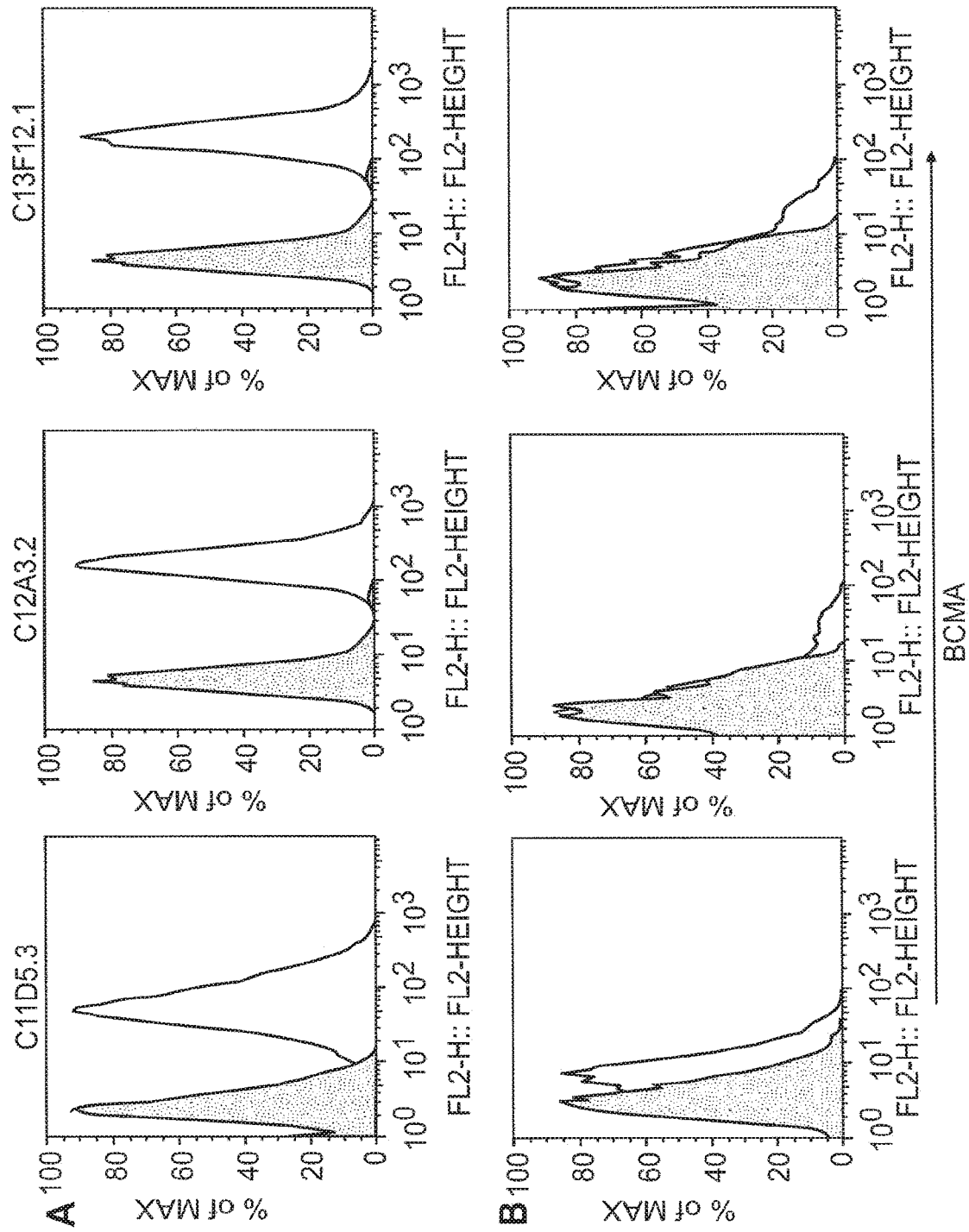
FIGS. 1A-1C depict binding of anti-human BCMA mAbs on BCMA-transfected CHO cells. Binding of biotin-conjugated anti-human BCMA mAbs, visualized with Streptavidin-PE, was measured by flow cytometry on a BCMA-CHO stable cell line (FIG. 1A) and control, non-transfected CHO cells (FIG. 1B). The shaded area represents staining of cells with an isotype control mAb.

| SEQ ID NO | Description of sequence |
|---|---|
| 1 | A7D12.2 mature heavy chain variable domain protein sequence |
| 2 | A7D12.2 mature light chain variable domain protein sequence |
| 3 | C11D5.3 mature heavy chain variable domain protein sequence |
| 4 | C11D5.3 mature light chain variable domain protein sequence A |
| 5 | C12A3.2 mature heavy chain variable domain protein sequence |
| 6 | C12A3.2 mature light chain variable domain protein sequence |
| 7 | C13F12.1 mature heavy chain variable domain protein sequence |
| 8 | C13F12.1 mature light chain variable domain protein sequence |
| 9 | BCMA protein sequence |
| 10 | huBCMA-huFc (as defined by N-terminal sequence analysis) |
| 11 | C11D5.3 mature light chain variable domain protein sequence B |
| 12 | C11D5.3 mature light chain variable domain protein sequence C |
| 13 | chA7D12.2 chimeric mature heavy chain protein sequence |
| 14 | chA7D12.2 chimeric mature light chain protein sequence |
| 15 | chC11D5.3 chimeric mature heavy chain protein sequence |
| 16 | chC11D5.3 chimeric mature light chain protein sequence A |
| 17 | chC11D5.3 chimeric mature light chain protein sequence C |
| 18 | chC12A3.2 chimeric mature heavy chain protein sequence |
| 19 | chC12A3.2 chimeric mature light chain protein sequence |
| 20 | chC13F12.1 chimeric mature heavy chain protein sequence |
| 21 | chC13F12.1 chimeric mature light chain protein sequence |
| 22 | huC11D5.3L1 humanized mature light chain variable domain sequence |
| 23 | huC11D5.3L2 humanized mature light chain variable domain sequence |
| 24 | huC11D5.3L3 humanized mature light chain variable domain sequence |
| 25 | huC11D5.3H0 humanized mature heavy chain variable domain sequence |
| 26 | huC11D5.3H1 humanized mature heavy chain variable domain sequence |
| 27 | huC11D5.3H2 humanized mature heavy chain variable domain sequence |
| 28 | huC11D5.3H3 humanized mature heavy chain variable domain sequence |
| 29 | huC11D5.3H4 humanized mature heavy chain variable domain sequence |
| 30 | huC12A3.2L0 humanized mature light chain variable domain sequence |
| 31 | huC12A3.2L1 humanized mature light chain variable domain sequence |
| 32 | huC12A3.2L2 humanized mature light chain variable domain sequence |
| 33 | huC12A3.2L3 humanized mature light chain variable domain sequence |
| 34 | huC12A3.2H0 humanized mature heavy chain variable domain sequence |
| 35 | huC12A3.2H1 humanized mature heavy chain variable domain sequence |
| 36 | huC12A3.2H2 humanized mature heavy chain variable domain sequence |
| 37 | huC12A3.2H3 humanized mature heavy chain variable domain sequence |
| 38 | huC12A3.2H4 humanized mature heavy chain variable domain sequence |
| 39 | huC13F12.1L0 humanized mature light chain variable domain sequence |
| 40 | huC13F12.1L1 humanized mature light chain variable domain sequence |

TABLE 1-continued

Brief Description of the Sequences

| SEQ ID NO | Description of sequence |
|---|---|
| 41 | huC13F12.1L2 humanized mature light chain variable domain sequence |
| 42 | huC13F12.1L3 humanized mature light chain variable domain sequence |
| 43 | huC13F12.1H0 humanized mature heavy chain variable domain sequence |
| 44 | huC13F12.1H1 humanized mature heavy chain variable domain sequence |
| 45 | huC13F12.1H2 humanized mature heavy chain variable domain sequence |
| 46 | huC13F12.1H3 humanized mature heavy chain variable domain sequence |
| 47 | huC13F12.1H4 humanized mature heavy chain variable domain sequence |

DETAILED DESCRIPTION OF THE EMBODIMENTS

The invention provides antibodies that bind to BCMA and certain epitopes thereof. In some embodiments, the antibodies of the invention bind to one or more subsets of B cells, such as plasma cells, memory B cells, and naïve B cells. The invention also provides methods of depleting B cells or subclasses of B cells, including plasma cells, memory B cells, and naïve B cells. In one embodiment, the invention provides an isolated antibody that binds to SEQ ID NO:9 and binds to plasma cells. In one embodiment, the invention provides an isolated antibody that binds to SEQ ID NO:9 and binds to memory B cells. In another embodiment, the invention provides an isolated antibody that binds to SEQ ID NO:9 and binds to naïve B cells.

Certain anti-BCMA mAbs, including clone C4E2.2 (hamster IgG) generated at Legacy Biogen (6); clone VICKY-1 (rat IgG1) (Alexis Biochemicals, Lausen, Switzerland, also sold as 6D10 by Santa Cruz Biotechnology, Santa Cruz, Calif.); and clone 335004 (rat IgG2a) (R&D Systems, Inc., Minneapolis, Minn.), are outside the scope of this invention.

A. Antibodies

The invention provides antibodies that bind specifically to SEQ ID NO:9. The invention also provides to antibodies that bind to the surface of B cells or subclasses thereof, including plasma cells, memory B cells (including switched, unswitched, and double negative), and/or naïve B cells. The term "antibody" as used herein, includes both full-length immunoglobulins and antibody fragments that bind to the same antigens. The antibodies can be, e.g., a monoclonal, polyclonal, chimeric, humanized, or single chain antibody. In some embodiments, the antibody fragments are Fab fragments or F(ab')2 fragments and retain the ability to specifically bind the protein of SEQ ID NO: 9.

In part, the invention provides the antibodies A7D12.2, C11D5.3, C12A3.2, and C13F12.1. Each of these is a murine monoclonal antibody. A7D12.2 has a murine "miscellaneous" subgroup heavy chain, a heavy chain variable domain sequence that is SEQ ID NO:1, a subgroup I kappa light chain, and a light chain variable domain sequence that is SEQ ID NO:2.

C11D5.3 has a subgroup II(A) heavy chain, a heavy chain variable domain sequence that is SEQ ID NO:3, a murine subgroup III kappa light chain, and a light chain variable domain sequence that is selected from SEQ ID NO:4, SEQ ID NO:11, and SEQ ID NO:12. In some embodiments, the light chain variable domain sequence of C11D5.3 is SEQ ID NO:12.

C12A3.2 has a subgroup II(A) heavy chain, a heavy chain variable domain sequence that is SEQ ID NO:5, a murine subgroup III kappa light chain, and a light chain variable domain sequence that is SEQ ID NO:6.

C13F12.1 has a subgroup II(A) heavy chain, a heavy chain variable domain sequence that is SEQ ID NO:7, a murine subgroup III kappa light chain, and a light chain variable domain sequence that is SEQ ID NO:8.

Techniques for producing single-chain antibodies specific to the protein of SEQ ID NO: 9 can be adapted from e.g., those described in U.S. Pat. No. 4,946,778. In addition, methods can be adapted for the construction of Fab expression libraries (see e.g., Huse et al. (1989) *Science* 246:1275-1281) to allow rapid and effective identification of monoclonal Fab fragments with the desired specificity for a BCMA protein or derivatives, fragments, analogs or homologs thereof. Numerous techniques for humanizing non-human antibodies are well known in the art. See e.g., U.S. Pat. Nos. 5,225,539, 6,632,927, or 5,648,237, all of which are incorporated by reference. Antibody fragments that contain the idiotypes to a BCMA protein may be produced by any of a variety of techniques, including, but not limited to: (i) an F(ab')2 fragment produced by pepsin digestion of an antibody molecule; (ii) an Fab fragment generated by reducing the disulfide bridges of an F(ab')2 fragment; (iii) a Fab fragment generated by the treatment of the antibody molecule with papain and a reducing agent and (iv) Fv fragments.

Additionally, recombinant anti-BCMA antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques such as, for example, the methods described in U.S. Pat. No. 7,112,421; Better et al. (1988) *Science* 240: 1041-1043; or Liu et ai. (1987) *Proc. Natl. Acad. Sci. USA* 84:3439-3443.

Some of the antibodies of the invention are chimeric forms of murine monoclonal antibodies A7D12.2, C11D5.3, C12A3.2, and C13F12.1. In some embodiments, a chimeric form of A7D12.2 comprises a heavy chain comprising SEQ ID NO:13 and a light chain comprising SEQ ID NO:14. In some embodiments, a chimeric form of C11D5.3 comprises a heavy chain comprising SEQ ID NO:15 and a light chain comprising a sequence selected from SEQ ID NO:16 and SEQ ID NO:17, preferably SEQ ID NO:17. In some embodiments, a chimeric form of C12A3.2 comprises a heavy chain comprising SEQ ID NO:18 and a light chain comprising SEQ ID NO:19. In some embodiments, a chimeric form of C13F12.1 comprises a heavy chain comprising SEQ ID NO:20 and a light chain comprising SEQ ID NO:21.

Some of the antibodies of the invention are humanized forms of murine monoclonal antibodies A7D12.2, C11D5.3, C12A3.2, and C13F12.1. In some embodiments, a humanized form of C11D5.3 comprises a light chain variable domain comprising a sequence that is at least 80%, at least 85%, at least 90%, at least 95%, or 100% identical to a sequence selected from SEQ ID NOs 22-24 and a heavy chain variable domain sequence comprising a sequence that is at least 80%, at least 85%, at least 90%, at least 95%, or 100% identical to a sequence selected from SEQ ID NOs 25-29. In some embodiments, a humanized form of C12A3.2 comprises a light chain variable domain comprising a sequence that is at least 80%, at least 85%, at least 90%, at least 95%, or 100% identical to a sequence selected from SEQ ID NOs 30-33 and a heavy chain variable domain sequence comprising a sequence that is at least 80%, at least 85%, at least 90%, at least 95%, or 100% identical to a sequence selected from SEQ ID NOs 34-38. In some embodiments, a humanized form of C13F12.1 comprises a light chain variable domain comprising a sequence that is at least 80%, at least 85%, at least 90%, at least 95%, or 100% identical to a sequence selected from SEQ ID NOs 39-42 and a heavy chain variable domain sequence comprising a sequence that is at least 80%, at least 85%, at least 90%, at least 95%, or 100% identical to a sequence selected from SEQ ID NOs 43-47.

B. Antibody Variable Domain Sequence

The antibodies of the invention may comprise the heavy chain variable domain sequences of SEQ ID NO:1, SEQ ID NO:3, SEQ ID NO:5, or SEQ ID NO:7. The heavy chain variable domain sequences may consist essentially of SEQ ID NO:1, SEQ ID NO:3, SEQ ID NO:5, or SEQ ID NO:7.

The antibodies of the invention may comprise the light chain variable domain sequences of SEQ ID NO:2, SEQ ID NO:4, SEQ ID NO:6, SEQ ID NO:8, SEQ ID NO:11, or SEQ ID NO:12. The light chain variable domain sequences may consist essentially of SEQ ID NO:2, SEQ ID NO:4, SEQ ID NO:6, SEQ ID NO:8, SEQ ID NO:11, or SEQ ID NO:12.

The invention also provides a variable domain sequence comprising a sequence that is at least 80%, at least 85%, at least 90%, or at least 95% identical to a sequence selected from SEQ ID NO:1, SEQ ID NO:3, SEQ ID NO:5, and SEQ ID NO:7. The invention also provides a variable domain sequence comprising a sequence that is at least 80%, at least 85%, at least 90%, or at least 95% identical to a sequence selected from SEQ ID NO:2, SEQ ID NO:4, SEQ ID NO:6, SEQ ID NO:8, SEQ ID NO:11, and SEQ ID NO:12. The invention also provides antibodies comprising a heavy chain variable domain sequence that is at least 80%, at least 85%, at least 90%, or at least 95% identical to SEQ ID NO:1 and a light chain variable domain sequence that is at least 80%, at least 85%, at least 90%, or at least 95% identical to SEQ ID NO:2. The invention includes antibodies comprising a heavy chain variable domain sequence that is at least 80%, at least 85%, at least 90%, or at least 95% identical to SEQ ID NO:3 and a light chain variable domain sequence that is at least 80%, at least 85%, at least 90%, or at least 95% identical to SEQ ID NO: 4, SEQ ID NO:11, or SEQ ID NO:12. The invention includes antibodies comprising a heavy chain variable domain sequence that is at least 80%, at least 85%, at least 90%, or at least 95% identical to SEQ ID NO:5 and a light chain variable domain sequence that is at least 80%, at least 85%, at least 90%, or at least 95% identical to SEQ ID NO:6. The invention includes antibodies comprising a heavy chain variable domain sequence that is at least 80%, at least 85%, at least 90%, or at least 95% identical to SEQ ID NO:7 and a light chain variable domain sequence that is at least 80%, at least 85%, at least 90%, or at least 95% identical to SEQ ID NO:8.

The invention also provides antibodies with particular complementarity determining regions (CDR). Table 2 defines the amino acid coordinates of CDR1, CDR2, and CDR3 of SEQ ID NOs:1 through 8, 11, and 12.

TABLE 2

CDR Amino Acid Coordinates

| SEQ ID NO | Description | CDR1 | CDR2 | CDR3 |
|---|---|---|---|---|
| 1 | A7D12.2 $V_H$ | 31-35 | 50-66 | 99-111 |
| 2 | A7D12.2 $V_L$ | 24-34 | 50-56 | 89-97 |
| 3 | C11D5.3 $V_H$ | 31-35 | 50-66 | 99-106 |
| 4 | C11D5.3 $V_L$ A | 24-38 | 54-60 | 93-101 |
| 5 | C12A3.2 $V_H$ | 31-35 | 50-66 | 99-106 |
| 6 | C12A3.2 $V_L$ | 24-38 | 54-60 | 93-101 |
| 7 | C13F12.1 $V_H$ | 31-35 | 50-66 | 99-106 |
| 8 | C13F12.1 $V_L$ | 24-38 | 54-60 | 93-101 |
| 11 | C11D5.3 $V_L$ B | 24-38 | 54-60 | 93-101 |
| 12 | C11D5.3 $V_L$ C | 24-38 | 54-60 | 93-101 |

CDRs are designated using the Kabat definitions (Johnson and Wu (2000), Nucleic Acids Res 28:214-218). As used herein, the "corresponding CDR" means the CDR in the most similar position within the variable domain amino acid sequence.

The heavy chain variable domain of antibodies of the invention may comprise CDRs such that one, two, or three of the CDRs are identical to the corresponding CDRs of SEQ ID NO:1; identical to the corresponding CDRs of SEQ ID NO:3; identical to the corresponding CDRs of SEQ ID NO:5; or identical to the corresponding CDRs of SEQ ID NO:7. The light chain variable domain of antibodies of the invention may comprise CDRs such that one, two, or three of the CDRs are identical to the corresponding CDRs of SEQ ID NO:2; identical to the corresponding CDRs of SEQ ID NO:4; identical to the corresponding CDRs of SEQ ID NO:6; identical to the corresponding CDRs of SEQ ID NO:8; identical to the corresponding CDRs of SEQ ID NO:11; or identical to the corresponding CDRs of SEQ ID NO:12.

The heavy chain variable domain may comprise CDRs identical to each of the corresponding CDRs of one of SEQ ID NO:1, SEQ ID NO:3, SEQ ID NO:5, or SEQ ID NO:7 except that one or more amino acid substitutions have been made in said CDR regions. In certain embodiments, CDRs of the heavy chain variable domain may have up to a total of 12 amino acid substitutions relative to SEQ ID NO:1, SEQ ID NO:3, SEQ ID NO:5, or SEQ ID NO:7. In other embodiments, the heavy chain variable domain CDRs of the antibodies of the invention may have up to 10, up to 8, up to 5, or up to 3 substitutions relative to SEQ ID NO:1, SEQ ID NO:3, SEQ ID NO:5, or SEQ ID NO:7. In some embodiments, the heavy chain variable domain CDRs of the antibodies of the invention are at least 80%, at least 85%, at least 90%, or at least 95% identical to the heavy chain variable domain CDRs of SEQ ID NO:1, SEQ ID NO:3, SEQ ID NO:5, or SEQ ID NO:7.

In some embodiments, CDR2 of SEQ ID NO:7 is replaced by CDR2 (i.e., amino acids 50-66) of SEQ ID NO:46. For example, the heavy chain variable domain of an antibody of the invention may comprise CDR1 and CDR3 of SEQ ID NO:7 and CDR2 of SEQ ID NO:46. The heavy chain variable domain of an antibody of the invention may also comprise CDR1, CDR2, and CDR3 regions that are together at least 80%, at least 85%, at least 90%, or at least 95% identical to CDR1 and CDR3 of SEQ ID NO:7 and CDR2 of SEQ ID NO:46.

The light chain variable domain may comprise CDRs identical to the corresponding CDRs of one of SEQ ID NO:2, SEQ ID NO:4, SEQ ID NO:6, SEQ ID NO:8, SEQ ID NO:11, or SEQ ID NO:12, except for one or more amino acid substitutions in said CDR regions. In certain embodiments, the antibodies of the invention comprise CDRs that are identical to the corresponding CDRs of one of SEQ ID NO:2, SEQ ID NO:4, SEQ ID NO:6, SEQ ID NO:8, SEQ ID NO:11, or SEQ ID NO:12, except for up to 12, up to 10, up to 8, up to 5, or up to 3 amino acid substitutions in said CDR regions. In some embodiments, the light chain variable domain CDRs of the antibodies of the invention are at least 80%, at least 85%, at least 90%, or at least 95% identical to the light chain variable domain CDRs of SEQ ID NO:2, SEQ ID NO:4, SEQ ID NO:6, SEQ ID NO:8, SEQ ID NO:11, or SEQ ID NO:12.

In some embodiments, the substitutions in the CDR regions are conservative substitutions.

C. Epitopes; Antibody Binding Specificity

The invention also provides antibodies that bind particular epitopes. Whether a pair of antibodies binds the same epitope is determined based on cross-blocking experiments, as described in Example 4. Cross-blocking profiles are defined for seven antibodies in Table 3. For the purposes of this disclosure, two antibodies are considered to bind to the same epitope if each one reduces the other's binding to BCMA (i.e., they mutually cross-block) by at least 90% according to the procedure described in Example 4. Similarly, antibodies that do not reduce each other's binding by at least 90% as described in Example 4 are considered to bind to distinct epitopes. The cross-blocking profiles of antibodies with certain variable domains are listed in Table 3. Pairs of antibodies that bind to distinct epitopes (as defined above) are noted with a "d."

extent of cross-blocking is measured according to the procedure described in Example 4.

In some embodiments, the antibodies and antibody fragments of the invention bind to the extracellular domain of BCMA. In particular embodiments, the antibodies bind to amino acids 1-52, 1-51, 1-41, or 8-41 of SEQ ID NO:9.

The invention also provides anti-BCMA antibodies that bind to one or more particular types of cell. The antibodies or antibody fragments of the invention may bind one or more of the following: plasma cells, memory B cells, naïve B cells, or cells that express BCMA (SEQ ID NO:9), a protein similar thereto, the extracellular domain thereof, or a polypeptide similar to the extracellular domain thereof.

D. Methods

The invention provides methods of depleting various types of cells. The methods comprise administering the antibodies of the invention, as described above. Types of cells that may be depleted by the methods of the invention include, without limitation, plasma cells, naïve B cells, memory B cells (including switched, unswitched, and double negative), lymphoma cells derived from B cells, and cells that express BCMA, a protein similar thereto, the extracellular domain thereof, or a polypeptide similar to the extracellular domain thereof. A cell may be in more than one of the foregoing categories. For an example of antibody-mediated cell depletion methods, see "Depletion of B Cells In Vivo by a Chimeric Mouse Human Monoclonal Antibody to CD20", Mitchell E. Reff, *Blood*, vol. 83, pp. 435-445, Jan. 15, 1994.

In some embodiments, treatment with an antibody of the invention reduces the number of one or more of the above-listed cell types by at least 25%, at least 30%, at least 35%, at least 40%, at least 45%, at least 50%, at least 60%, at least 70%, at least 75%, at least 80%, and least 85%, at least 90%, or at least 95%. In some embodiments, treatment with an antibody of the invention reduces the number of plasma cells by at least 25%, at least 30%, at least 35%, at least 40%, at least 45%, 50%, at least 60%, at least 70%, at least 75%, at

TABLE 3

Cross-Blocking Profiles

| Heavy chain var. domain SEQ ID NO | Light chain var. domain SEQ ID NO | Example | Distinct (d) from epitope bound by: | | | | | | |
|---|---|---|---|---|---|---|---|---|---|
| | | | C12A3.2 | C11D5.3 | C13F12.1 | 335004 | C4E2 | A7D12.2 | VICKY-1 |
| 1 | 2 | A7D12.2 | d | d | d | d | d | — | d |
| 3 | 12 | C11D5.3 | — | — | — | d | d | d | d |
| 5 | 6 | C12A3.2 | — | — | — | d | d | d | d |
| 7 | 8 | C13F12.1 | — | — | — | d | d | d | d |

The invention further encompasses antibodies that bind to the same epitope as antibodies A7D12.2, C11D5.3, C12A3.2, or C13F12.1. The invention also provides antibodies that have cross-blocking profiles that match the profiles of A7D12.2, C11D5.3, C12A3.2, or C13F12.1. For example, following the definitions provided above, an antibody that has the same profile as C11D5.3 binds to the same epitope as compared to C12A3.2 and C13F12.1 but binds to a distinct epitope as compared to A7D12.2, 335004, C4E2, and Vicky-1. In some embodiments, the antibodies of the invention mutually cross-block one or more of A7D12.2, C11D5.3, C12A3.2, or C13F12.1 from binding the protein of SEQ ID NO: 9 by at least 80%, 85%, 90%, or 95%. The least 80%, at least 85%, at least 90%, or at least 95%. In some embodiments, treatment with an antibody of the invention reduces the number of switched memory B cells by at least 25%, at least 30%, at least 35%, at least 40%, at least 45%, at least 50%, or at least 60%. In some embodiments, treatment with an antibody of the invention reduces the number of unswitched memory B cells by at least 25%, at least 30%, at least 35%, at least 40%, at least 45%, at least 50%, or at least 60%. In some embodiments, treatment with an antibody of the invention reduces the number of double negative memory B cells by at least 25%, at least 30%, at least 35%, at least 40%, at least 45%, at least 50%, or at least 60%. In some embodiments, treatment with an antibody of the invention reduces the number of naive B cells by at least 25%, at least 30%, at least 35%, at least 40%, at least 45%, at least 50%, or at least 60%.

The invention also provides methods of reducing serum immunoglobulin levels comprising administering an antibody of the invention. In some embodiments, such methods reduce serum IgM levels. In particular embodiments, treatment with an antibody of the invention reduces serum IgM levels by at least 25%, at least 30%, at least 35%, at least 40%, at least 45%, at least 50%, at least 55%, at least 60%, or at least 65%. In some embodiments, such methods reduce serum IgG levels. In some embodiments, such methods reduce the levels of one or both of IgG2 and IgG3. In some embodiments, such methods reduce the levels of IgG2 by at least 25%, at least 30%, at least 35%, at least 40%, at least 50%, at least 60%, at least 65%, or at least 70%. In some embodiments, such methods reduce the levels of IgG3 by at least 25%, at least 30%, at least 35%, at least 40%, at least 50%, at least 60%, at least 65%, at least 70%, at least 75%, or at least 80%. In some embodiments, such methods reduce IgG2, IgG3, and IgM levels.

The invention also provides methods of reducing the level of at least one autoantibody comprising administering an antibody of the invention. In some embodiments, such methods reduce the level of one or more autoantibodies by at least 25%, at least 30%, at least 35%, at least 40%, at least 45%, at least 50%, at least 60%, at least 70%, at least 75%, at least 80%, and least 85%, at least 90%, or at least 95%.

In a still further aspect, the invention provides methods of treating or preventing or delaying a B-cell mediated condition disorder. The method includes administering to a subject in which such treatment or prevention or delay is desired, an antibody of the invention in an amount sufficient to treat, prevent, or delay a tumorigenic or immunoregulatory condition in the subject. In some embodiments, the subject is a human. In other embodiments, the subject is a non-human mammal. In some embodiments, administration of the antibody of the invention blocks BCMA-mediated signalling in the subject, which may result in one or more of cell death, inhibition, reduction, or cessation of cell proliferation.

In some embodiments, the antibodies or antibody fragments of the invention use BCMA to "target" B cell lymphomas. In essence, such targeting can be generalized as follows: antibodies or antibody fragments of the invention specific to the BCMA surface antigen of B cells are, e.g., injected into a subject and specifically bind to the BCMA cell surface antigen of (ostensibly) both normal and malignant B cells; this binding leads to the destruction and/or depletion of neoplastic B cells. Additionally, chemical agents or radioactive labels having the potential to destroy cancer cells and/or tumors can be conjugated to the antibodies or antibody fragments of the invention such that the agent is specifically "delivered" to the targeted B cells, such as, e.g., neoplastic B cells. In some embodiments, the methods of the invention comprise administering an antibody or antibody fragment that is not conjugated to a chemical agent or radioactive label. In some embodiments, the methods of the invention comprise administering an antibody or antibody fragment that is not conjugated to a cytotoxic agent.

B cell-related disorders include, without limitation, autoimmune diseases involving inappropriate B cell activity and B cell lymphomas. B cell lymphomas include, without limitation, multiple myeloma, plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, and small lymphocytic lymphoma. The antibodies or antibody fragments of the invention may also be used to treat cancers in which the cancer cells express BCMA. The B cell-related disorders additionally include B cell proliferations of uncertain malignant potential, such as, for example, lymphomatoid granulomatosis and post-transplant lymphoproliferative disorder.

The conditions diagnosed, treated, prevented or delayed using the antibodies or antibody fragments of the invention can additionally be an immunoregulatory disorder. These disorders include those that are autoimmune in nature such as, for example, systemic lupus erythematosus, rheumatoid arthritis, myasthenia gravis, autoimmune hemolytic anemia, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, and rapidly progressive glomerulonephritis. The antibodies or antibody fragments of the invention may also have application in plasma cell disorders such as heavy-chain disease, primary or immunocyte-associated amyloidosis, and monoclonal gammopathy of undetermined significance (MGUS).

Compositions and methods of treatment using the antibodies or antibody fragments of the invention can be used with any condition associated with undesired BCMA-expressing cell proliferation.

The antibodies of the invention may also be administered in conjunction with antibody C2B8 of U.S. Pat. No. 5,736,137, also known as RITUXAN™. In some embodiments, such combined administration depletes or inhibits the proliferation of multiple B cell subtypes.

The invention further provides for the use of the antibodies of the invention to assay B cell phenotypes, such as determination of the presence, absence, or amount of a marker on the surface of a B cell or B cell subtype. For example, the antibodies of the invention may be used to measure the presence of a marker associated with SLE or another B cell-related condition on the surface of naïve B cells, memory B cells, IgD+ memory B cells, IgD− memory B cells, or double negative memory B cells.

E. Pharmaceutical Compositions

The antibodies of the invention can be incorporated into pharmaceutical compositions suitable for administration. Such compositions typically comprise antibodies and a pharmaceutically acceptable carrier. As used herein, "pharmaceutically acceptable carrier" is intended to include any and all solvents, dispersion media, coatings, antibacterial and antifungal agents, isotonic and absorption delaying agents, diluents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the antibodies, use thereof in the compositions is contemplated. Supplementary active compounds can also be incorporated into the compositions.

A pharmaceutical composition comprising antibodies of the invention is formulated to be compatible with its intended route of administration. Examples of routes of administration include parenteral, e.g., intravenous, intradermal, subcutaneous, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating antibodies of the invention in the required amount in an appropriate solvent with one or a combination of ingredients enumerated above, as required, followed by filtered sterilization. Generally, dispersions are prepared by incorporating the antibodies into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the antibodies plus any additional desired ingredient from a previously sterile-filtered solution thereof.

In one embodiment, the antibodies are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. Additionally, the antibodies or antibody fragments of the invention may be used to target liposomal suspensions to B cells or subclasses thereof to which the particular antibody binds. These can be prepared according to methods known to those skilled in the art, for example, as described in U.S. Pat. No. 4,522,811.

Parenteral compositions may be formulated in dosage unit form for ease of administration and uniformity of dosage. Dosage unit form as used herein refers to physically discrete units suited as unitary dosages for the subject to be treated; each unit containing a predetermined quantity of antibody calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions comprising an antibody of the invention can be included in a container, pack, or dispenser together with instructions for administration.

F. Listing of Exemplary Embodiments

1. An isolated antibody that binds to SEQ ID NO:9 and binds to memory B cells.
2. The antibody of embodiment 1, wherein the antibody also binds to plasma cells.
3. The antibody of embodiment 1, wherein the antibody also binds to naïve B cells.
4. The antibody of embodiment 1, wherein the antibody also binds to naïve B cells and plasma cells.
5. A method of depleting naïve B cells, memory B cells, and plasma cells, comprising administering an antibody that binds to SEQ ID NO:9 and binds to naïve B cells, memory B cells, and plasma cells.
6. A method of depleting memory B cells, comprising administering an antibody that binds to SEQ ID NO:9 and binds to memory B cells.
7. An isolated antibody that binds to SEQ ID NO:9 and binds to naïve B cells.
8. The antibody of embodiment 7, wherein the antibody binds to plasma cells.
9. A method of depleting naïve B cells, comprising administering an antibody that binds to SEQ ID NO:9 and binds to naïve B cells.
10. An isolated antibody that binds to the polypeptide of SEQ ID NO:9, wherein the antibody comprises at least one CDR chosen from CDR1, CDR2, or CDR3 of a protein sequence selected from the group consisting of SEQ ID NO:1, SEQ ID NO:3, SEQ ID NO:5, and SEQ ID NO:7.
11. The antibody of embodiment 10, wherein the antibody comprises at least two CDRs chosen from CDR1, CDR2, or CDR3 of a protein sequence selected from the group consisting of SEQ ID NO:1, SEQ ID NO:3, SEQ ID NO:5, and SEQ ID NO:7.

12. The antibody of embodiment 10, wherein the antibody comprises the CDRs at CDR1, CDR2, and CDR3 of a protein sequence selected from the group consisting of SEQ ID NO:1, SEQ ID NO:3, SEQ ID NO:5, and SEQ ID NO:7.

13. The antibody of embodiment 10, wherein the at least one CDR chosen from CDR1, CDR2, or CDR3 is from SEQ ID NO: 1, and the antibody further comprises a variable domain comprising at least one of a CDR1 region identical to amino acids 24-34 of SEQ ID NO:2, a CDR2 region identical to amino acids 50-56 of SEQ ID NO:2, or a CDR3 region identical to amino acids 89-97 of SEQ ID NO:2.

14. The antibody of embodiment 10, wherein the at least one CDR chosen from CDR1, CDR2, or CDR3 is from SEQ ID NO: 3, and the antibody further comprises a variable domain comprising at least one of a CDR1 region identical to amino acids 24-38 of SEQ ID NO: 12, a CDR2 region identical to amino acids 54-60 of SEQ ID NO: 12, or a CDR3 region identical to amino acids 93-101 of SEQ ID NO: 12.

15. The antibody of embodiment 10, wherein the at least one CDR chosen from CDR1, CDR2, or CDR3 is from SEQ ID NO: 5, and the antibody further comprises a variable domain comprising at least one of a CDR1 region identical to amino acids 24-38 of SEQ ID NO: 6, a CDR2 region identical to amino acids 54-60 of SEQ ID NO: 6, or a CDR3 region identical to amino acids 93-101 of SEQ ID NO: 6.

16. The antibody of embodiment 10, wherein the at least one CDR chosen from CDR1, CDR2, or CDR3 is from SEQ ID NO: 7, and the antibody further comprises a variable domain comprising at least one of a CDR1 region identical to amino acids 24-38 of SEQ ID NO: 8, a CDR2 region identical to amino acids 54-60 of SEQ ID NO: 8, or a CDR3 region identical to amino acids 93-101 of SEQ ID NO: 8.

17. The antibody of embodiment 10, wherein the heavy chain variable domain comprises SEQ ID NO:1 and the light chain variable domain comprises SEQ ID NO:2.

18. The antibody of embodiment 10, wherein the heavy chain variable domain comprises SEQ ID NO:3 and the light chain variable domain comprises SEQ ID NO:12.

19. The antibody of embodiment 10, wherein the heavy chain variable domain comprises SEQ ID NO:5 and the light chain variable domain comprises SEQ ID NO:6.

20. The antibody of embodiment 10, wherein the heavy chain variable domain comprises SEQ ID NO:7 and the light chain variable domain comprises SEQ ID NO:8.

21. An isolated antibody that binds the same epitope as the antibody of embodiment 17.

22. An isolated antibody that binds the same epitope as the antibody of any of embodiments 18-20.

23. An isolated antibody that binds to the polypeptide of SEQ ID NO:9, wherein the antibody comprises:
   a. a variable domain comprising CDR1, CDR2, and CDR3 regions identical to the CDR1, CDR2, and CDR3 of a sequence which is chosen from SEQ ID NO:1, SEQ ID NO:3, SEQ ID NO:5, or SEQ ID NO:7; or
   b. a variant of the variable domain of part (a) that is otherwise identical to said variable domain except for up to a total of 10 amino acid substitutions in said CDR regions.

24. The antibody of embodiment 53, wherein the sequence is SEQ ID NO:1 and the antibody further comprises:
   c. a variable domain comprising a CDR1 region identical to amino acids 24-34 of SEQ ID NO:2, a CDR2 region identical to amino acids 50-56 of SEQ ID NO:2, and a CDR3 region identical to amino acids 89-97 of SEQ ID NO:2; or
   d. a variant of the variable domain of part (c) that is otherwise identical to said variable domain except for up to a total of 10 amino acid substitutions in said CDR regions.

25. The antibody of embodiment 53, wherein the sequence is SEQ ID NO:3 and the antibody further comprises:
   c. a variable domain comprising a CDR1 region identical to amino acids 24-38 of SEQ ID NO:12, a CDR2 region identical to amino acids 54-60 of SEQ ID NO:12, and a CDR3 region identical to amino acids 93-101 of SEQ ID NO:12; or
   d. a variant of the variable domain of part (c) that is otherwise identical to said variable domain except for up to a total of 10 amino acid substitutions in said CDR regions.

26. The antibody of embodiment 53, wherein the sequence is SEQ ID NO:5 and the antibody further comprises:
   c. a variable domain comprising a CDR1 region identical to amino acids 24-38 of SEQ ID NO:6, a CDR2 region identical to amino acids 54-60 of SEQ ID NO:6, and a CDR3 region identical to amino acids 93-101 of SEQ ID NO:6; or
   d. a variant of the variable domain of part (c) that is otherwise identical to said variable domain except for up to a total of 10 amino acid substitutions in said CDR regions.

27. The antibody of embodiment 53, wherein the sequence is SEQ ID NO:7 and the antibody further comprises:
   c. a variable domain comprising a CDR1 region identical to amino acids 24-38 of SEQ ID NO:8, a CDR2 region identical to amino acids 54-60 of SEQ ID NO:8, and a CDR3 region identical to amino acids 93-101 of SEQ ID NO:8; or
   d. a variant of the variable domain of part (c) that is otherwise identical to said variable domain except for up to a total of 10 amino acid substitutions in said CDR regions.

28. An isolated antibody that binds to the polypeptide of SEQ ID NO:9, wherein the antibody comprises at least one CDR chosen from CDR1, CDR2, or CDR3 of a protein sequence selected from the group consisting of SEQ ID NO:2, SEQ ID NO:4, SEQ ID NO:6, SEQ ID NO:8; SEQ ID NO:11; and SEQ ID NO:12.

29. The antibody of embodiment 28, wherein the antibody comprises at least two CDRs chosen from CDR1, CDR2, or CDR3 of a protein sequence selected from the group consisting of SEQ ID NO:2, SEQ ID NO:12, SEQ ID NO:6, and SEQ ID NO:8.

30. The antibody of embodiment 28, wherein the antibody comprises the CDRs at CDR1, CDR2, and CDR3 of a protein sequence selected from the group consisting of SEQ ID NO:2, SEQ ID NO:12, SEQ ID NO:6, or SEQ ID NO:8.

31. The antibody of any of embodiments 1-4, 7, 8, 10-21, or 23-30, wherein the antibody is a chimeric, humanized, or single chain antibody.

32. A hybridoma that produces the antibody of any of embodiments 1-4, 7, 8, 10-21, or 23-30.

33. A pharmaceutical composition comprising the antibody of any of embodiments 1-4, 7, 8, 10-21, or 23-30 and a pharmaceutically acceptable carrier.

34. A polypeptide that binds to SEQ ID NO:9 and comprises the antigen binding portion, Fab fragment, or F(ab')2 fragment of the antibody of any of embodiments 1-4, 7, 8, 10-21, or 23-30.

35. A hybridoma that produces the antigen binding portion, Fab fragment, or F(ab')2 fragment of embodiment 33.

36. A pharmaceutical composition comprising the antigen binding portion, Fab fragment, or F(ab')2 fragment of embodiment 33 and a pharmaceutically acceptable carrier.

37. A method of depleting plasma cells, comprising administering the antibody of any of embodiments 1-4, 8, or 10-31.

38. A method of treating a B cell-related disorder, comprising administering the antibody of any one of embodiments 1-4, 8, or 10-31.

39. The method of embodiment 38, wherein the B-cell related disorder is plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, small lymphocytic lymphoma, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy of undetermined significance.

40. The method of embodiment 38, wherein the B cell-related disorder is a B cell malignancy.

41. The method of embodiment 38, wherein the B cell-related disorder is a plasma cell malignancy.

42. The method of embodiment 41, wherein the plasma cell malignancy is multiple myeloma.

43. The method of embodiment 38, wherein the B cell-related disorder is an autoimmune disease.

44. The method of embodiment 43, wherein the autoimmune disease is systemic lupus erythematosus.

45. The antibody of embodiment 10, wherein the at least one CDR chosen from CDR1, CDR2, or CDR3 is from SEQ ID NO: 1, and the antibody further comprises a variable domain comprising at least two of a CDR1 region identical to amino acids 24-34 of SEQ ID NO:2, a CDR2 region identical to amino acids 50-56 of SEQ ID NO:2, or a CDR3 region identical to amino acids 89-97 of SEQ ID NO:2.

46. The antibody of embodiment 10, wherein the at least one CDR chosen from CDR1, CDR2, or CDR3 is from SEQ ID NO: 1, and the antibody further comprises a variable domain comprising a CDR1 region identical to amino acids 24-34 of SEQ ID NO:2, a CDR2 region identical to amino acids 50-56 of SEQ ID NO:2, and a CDR3 region identical to amino acids 89-97 of SEQ ID NO:2.

47. The antibody of embodiment 10, wherein the at least one CDR chosen from CDR1, CDR2, or CDR3 is from SEQ ID NO: 3, and the antibody further comprises a variable domain comprising at least two of a CDR1 region identical to amino acids 24-38 of SEQ ID NO: 12, a CDR2 region identical to amino acids 54-60 of SEQ ID NO: 12, or a CDR3 region identical to amino acids 93-101 of SEQ ID NO: 12.

48. The antibody of embodiment 10, wherein the at least one CDR chosen from CDR1, CDR2, or CDR3 is from SEQ ID NO: 3, and the antibody further comprises a variable domain comprising a CDR1 region identical to amino acids 24-38 of SEQ ID NO: 12, a CDR2 region identical to amino acids 54-60 of SEQ ID NO: 12, and a CDR3 region identical to amino acids 93-101 of SEQ ID NO: 12.

49. The antibody of embodiment 10, wherein the at least one CDR chosen from CDR1, CDR2, or CDR3 is from SEQ ID NO: 5, and the antibody further comprises a variable domain comprising at least two of a CDR1 region identical to amino acids 24-38 of SEQ ID NO: 6, a CDR2 region identical to amino acids 54-60 of SEQ ID NO: 6, or a CDR3 region identical to amino acids 93-101 of SEQ ID NO: 6.

50. The antibody of embodiment 10, wherein the at least one CDR chosen from CDR1, CDR2, or CDR3 is from SEQ ID NO: 5, and the antibody further comprises a variable domain comprising a CDR1 region identical to amino acids 24-38 of SEQ ID NO: 6, a CDR2 region identical to amino acids 54-60 of SEQ ID NO: 6, and a CDR3 region identical to amino acids 93-101 of SEQ ID NO: 6.

51. The antibody of embodiment 10, wherein the at least one CDR chosen from CDR1, CDR2, or CDR3 is from SEQ ID NO: 7, and the antibody further comprises a variable domain comprising at least two of a CDR1 region identical to amino acids 24-38 of SEQ ID NO: 8, a CDR2 region identical to amino acids 54-60 of SEQ ID NO: 8, or a CDR3 region identical to amino acids 93-101 of SEQ ID NO: 8.

52. The antibody of embodiment 10, wherein the at least one CDR chosen from CDR1, CDR2, or CDR3 is from SEQ ID NO: 7, and the antibody further comprises a variable domain comprising a CDR1 region identical to amino acids 24-38 of SEQ ID NO: 8, a CDR2 region identical to amino acids 54-60 of SEQ ID NO: 8, and a CDR3 region identical to amino acids 93-101 of SEQ ID NO: 8.

53. The antibody of embodiment 10, wherein the antibody comprises at least two CDRs chosen from CDR1, CDR2, or CDR3 of SEQ ID NO:1 and at least one CDR chosen from CDR1, CDR2, or CDR3 of SEQ ID No:2.

54. The antibody of embodiment 10, wherein the antibody comprises at least two CDRs chosen from CDR1, CDR2, or CDR3 of SEQ ID NO:3 and at least one CDR chosen from CDR1, CDR2, or CDR3 of SEQ ID No:12.

55. The antibody of embodiment 10, wherein the antibody comprises at least two CDRs chosen from CDR1, CDR2, or CDR3 of SEQ ID NO:5 and at least one CDR chosen from CDR1, CDR2, or CDR3 of SEQ ID No:6.

56. The antibody of embodiment 10, wherein the antibody comprises at least two CDRs chosen from CDR1, CDR2, or CDR3 of SEQ ID NO:7 and at least one CDR chosen from CDR1, CDR2, or CDR3 of SEQ ID No:8.

57. The antibody of embodiment 10, wherein the antibody comprises CDRs that are CDR1, CDR2, and CDR3 of SEQ ID NO:1 and at least one CDR chosen from CDR1, CDR2, or CDR3 of SEQ ID No:2.

58. The antibody of embodiment 10, wherein the antibody comprises CDRs that are CDR1, CDR2, or CDR3 of SEQ ID NO:3 and at least one CDR chosen from CDR1, CDR2, or CDR3 of SEQ ID No:12.

59. The antibody of embodiment 10, wherein the antibody comprises CDRs that are CDR1, CDR2, or CDR3 of SEQ ID NO:5 and at least one CDR chosen from CDR1, CDR2, or CDR3 of SEQ ID No:6.

60. The antibody of embodiment 10, wherein the antibody comprises CDRs that are CDR1, CDR2, or CDR3 of SEQ ID NO:7 and at least one CDR chosen from CDR1, CDR2, or CDR3 of SEQ ID No:8.

61. The antibody of embodiment 10, wherein the antibody comprises at least two CDRs chosen from CDR1, CDR2, or CDR3 of SEQ ID NO:1 and at least two CDRs chosen from CDR1, CDR2, or CDR3 of SEQ ID No:2.

62. The antibody of embodiment 10, wherein the antibody comprises at least two CDRs chosen from CDR1, CDR2, or CDR3 of SEQ ID NO:3 and at least two CDRs chosen from CDR1, CDR2, or CDR3 of SEQ ID No:12.

63. The antibody of embodiment 10, wherein the antibody comprises at least two CDRs chosen from CDR1, CDR2, or CDR3 of SEQ ID NO:5 and at least two CDRs chosen from CDR1, CDR2, or CDR3 of SEQ ID No:6.

64. The antibody of embodiment 10, wherein the antibody comprises at least two CDRs chosen from CDR1, CDR2, or CDR3 of SEQ ID NO:7 and at least two CDRs chosen from CDR1, CDR2, or CDR3 of SEQ ID No:8.

65. The antibody of embodiment 10, wherein the antibody comprises CDRs that are CDR1, CDR2, and CDR3 of SEQ ID NO:1 and at least two CDRs chosen from CDR1, CDR2, or CDR3 of SEQ ID No:2.

66. The antibody of embodiment 10, wherein the antibody comprises CDRs that are CDR1, CDR2, or CDR3 of SEQ ID NO:3 and at least two CDRs chosen from CDR1, CDR2, or CDR3 of SEQ ID No:12.

67. The antibody of embodiment 10, wherein the antibody comprises CDRs that are CDR1, CDR2, or CDR3 of SEQ ID NO:5 and at least two CDRs chosen from CDR1, CDR2, or CDR3 of SEQ ID No:6.

68. The antibody of embodiment 10, wherein the antibody comprises CDRs that are CDR1, CDR2, or CDR3 of SEQ ID NO:7 and at least two CDRs chosen from CDR1, CDR2, or CDR3 of SEQ ID No:8.

69. The antibody of embodiment 10, wherein the antibody comprises at least two CDRs chosen from CDR1, CDR2, or CDR3 of SEQ ID NO:1 and CDRs that are CDR1, CDR2, or CDR3 of SEQ ID No:2.

70. The antibody of embodiment 10, wherein the antibody comprises at least two CDRs chosen from CDR1, CDR2, or CDR3 of SEQ ID NO:3 and CDRs that are CDR1, CDR2, or CDR3 of SEQ ID No:12.

71. The antibody of embodiment 10, wherein the antibody comprises at least two CDRs chosen from CDR1, CDR2, or CDR3 of SEQ ID NO:5 and CDRs that are CDR1, CDR2, or CDR3 of SEQ ID No:6.

72. The antibody of embodiment 10, wherein the antibody comprises at least two CDRs chosen from CDR1, CDR2, or CDR3 of SEQ ID NO:7 and CDRs that are CDR1, CDR2, or CDR3 of SEQ ID No:8.

73. The antibody of embodiment 10, wherein the antibody comprises CDRs that are CDR1, CDR2, and CDR3 of SEQ ID NO:1 and CDRs that are CDR1, CDR2, or CDR3 of SEQ ID No:2.

74. The antibody of embodiment 10, wherein the antibody comprises CDRs that are CDR1, CDR2, or CDR3 of SEQ ID NO:3 and CDRs that are CDR1, CDR2, or CDR3 of SEQ ID No:12.

75. The antibody of embodiment 10, wherein the antibody comprises CDRs that are CDR1, CDR2, or CDR3 of SEQ ID NO:5 and CDRs that are CDR1, CDR2, or CDR3 of SEQ ID No:6.

76. The antibody of embodiment 10, wherein the antibody comprises CDRs that are CDR1, CDR2, or CDR3 of SEQ ID NO:7 and CDRs that are CDR1, CDR2, or CDR3 of SEQ ID No:8.

77. An isolated antibody that mutually cross-blocks the antibody of embodiment 17 by at least 80%.

78. An isolated antibody that mutually cross-blocks at least one of the antibodies of embodiments 18-20 by at least 80%.

79. An isolated antibody that binds to the same epitope as the antibody of embodiment 18.

80. An isolated antibody that binds to the same epitope as the antibody of embodiment 19.

81. An isolated antibody that binds to the same epitope as the antibody of embodiment 20.

82. A method of reducing the level of at least one autoantibody, comprising administering the antibody of any of embodiments 1-4, 8, and 10-31.

83. A method of reducing serum IgM level, comprising administering the antibody of any of embodiments 1-4, 8, and 10-31.

84. A method of reducing serum IgG level, comprising administering the antibody of any of embodiments 1-4, 8, and 10-31.

85. A method of reducing serum IgG2 level, comprising administering the antibody of any of embodiments 1-4, 8, and 10-31.

86. A method of reducing serum IgG3 level, comprising administering the antibody of any of embodiments 1-4, 8, and 10-31.

87. An isolated antibody that binds to the polypeptide of SEQ ID NO:9, wherein the antibody comprises a variable domain comprising CDR1, CDR2, and CDR3 regions that are together at least 95% identical to the CDR1, CDR2, and CDR3 regions of a sequence which is chosen from SEQ ID NO:1, SEQ ID NO:3, SEQ ID NO:5, or SEQ ID NO:7.

88. The antibody of embodiment 87, wherein the sequence is SEQ ID NO:1 and the antibody further comprises a variable domain comprising CDR1, CDR2, and CDR3 regions that are together at least 95% identical to the CDR1, CDR2, and CDR3 regions of SEQ ID NO:2.

89. The antibody of embodiment 87, wherein the sequence is SEQ ID NO:3 and the antibody further comprises a variable domain comprising CDR1, CDR2, and CDR3 regions that are together at least 95% identical to the CDR1, CDR2, and CDR3 regions of SEQ ID NO:12.

90. The antibody of embodiment 87, wherein the sequence is SEQ ID NO:5 and the antibody further comprises a variable domain comprising CDR1, CDR2, and CDR3 regions that are together at least 95% identical to the CDR1, CDR2, and CDR3 regions of SEQ ID NO:6.

91. The antibody of embodiment 87, wherein the sequence is SEQ ID NO:7 and the antibody further comprises a variable domain comprising CDR1, CDR2, and CDR3 regions that are together at least 95% identical to the CDR1, CDR2, and CDR3 regions of SEQ ID NO:8.

92. An isolated antibody that binds to the polypeptide of SEQ ID NO:9, wherein the antibody comprises a light chain variable domain comprising a sequence that is at least 95% identical to a sequence selected from SEQ ID NOs 22-24 and a heavy chain variable domain sequence comprising a sequence that is at least 95% identical to a sequence selected from SEQ ID NOs 25-29.

93. An isolated antibody that binds to the polypeptide of SEQ ID NO:9, wherein the antibody comprises a light chain variable domain comprising a sequence that is at least 95% identical to a sequence selected from SEQ ID NOs 30-33 and a heavy chain variable domain sequence comprising a sequence that is at least 95% identical to a sequence selected from SEQ ID NOs 34-38.

94. An isolated antibody that binds to the polypeptide of SEQ ID NO:9, wherein the antibody comprises a light chain variable domain comprising a sequence that is at least 95% identical to a sequence selected from SEQ ID NOs 39-42 and a heavy chain variable domain sequence comprising a sequence that is at least 95% identical to a sequence selected from SEQ ID NOs 43-47.

95. The method of embodiment 39, wherein the B-cell related disorder is rheumatoid arthritis.
96. The method of embodiment 39, wherein the B-cell related disorder is idiopathic thrombocytopenia purpura, or myasthenia gravis, or autoimmune hemolytic anemia.
97. The method of embodiment 37, further comprising administering RITUXAN™
98. The method of embodiment 38, further comprising administering RITUXAN™

Example 1. Generation and Biotin Conjugation of Anti-Human BCMA Monoclonal Antibodies Anti-BCMA monoclonal antibodies (mAbs) were generated by immunizing female RBF mice with BCMA-Fc/KLH conjugate protein i.p. in CFA, followed by additional immunizations at regular intervals with IFA, except that the last boost used RIBI instead of IFA, prior to splenocyte fusion to the FL653 myeloma cell line after the method of Harlow and Lane (1998), *Using Antibodies: A Laboratory Manual: Portable Protocol No. I*, Cold Spring Harbor Laboratory, Cold Spring Harbor, N.Y. Briefly, splenocytes isolated from a mouse 3 days after the final boost were washed twice and mixed in a 7:1 ratio with twice-washed log phase FL653 myeloma cells. The cell mixture was split four ways, pelleted, and incubated in 37° C. PEG for 1 min during which time cells were gently resuspended, followed by careful addition of 10 ml ice-cold DMEM. Cells were mixed, pelleted, and resuspended in AAT hybridoma growth selection media. Cell supernatants were screened for BCMA-specific reactivity by ELISA and flow cytometry. Clones that scored positive for BCMA and negative for Fc-specificity in an ELISA format, positive on BCMA-transfected cells, and negative on mock-transfected cells were expanded and subcloned. Four BCMA-specific clones were selected for further evaluation: C11D5.3 (IgG1), C12A3.2 (IgG1), C13F12.1 (IgG1) and A7D12.2 (IgG2b). Anti-BCMA mAbs were biotin-conjugated for use in ELISA and FACS experiments described below using a kit according to the manufacturer's recommendations (Molecular Probes, Eugene, Oreg.).

Example 2. Cloning of Murine Anti-Human BCMA mAb Variable Regions

Total cellular RNA from murine hybridoma cells was prepared using a Qiagen RNeasy mini kit following the manufacturer's recommended protocol. cDNAs encoding the variable regions of the heavy and light chains were cloned by RT-PCR from total cellular RNA, using random hexamers for priming of first strand cDNA. For PCR amplification of the murine immunoglobulin variable domains with intact signal sequences, a cocktail of degenerate forward primers hybridizing to multiple murine immunoglobulin gene family signal sequences and a single back primer specific for the 5' end of the murine constant domain were used. PCR was performed using Clontech Advantage 2 Polymerase mix following the manufacturer's recommended protocol. The PCR products were gel-purified and subcloned into Invitrogen's pCR2.1TOPO vector using their TOPO cloning kit following the manufacturer's recommended protocol. Inserts from multiple independent subclones were sequenced to establish a consensus sequence. Deduced mature immunoglobulin N-termini were consistent with those determined by Edman degradation from the hybridoma. Assignment to specific subgroups was based upon BLAST analysis using consensus immunoglobulin variable domain sequences from the Kabat database (Johnson and Wu (2000), Nucleic Acids Res 28:214-218). CDRs were designated using the Kabat definitions (Johnson and Wu (2000), Nucleic Acids Res 28:214-218).

Example 3. Stable BCMA-Expressing CHO Cell Line Development and Assessment of Anti-Human BCMA mAbs To validate specific binding to BCMA, anti-BCMA mAbs were screened on a stable BCMA-expressing CHO cell line. The stable BCMA-expressing CHO cell line was generated using a previously described method (Brezinsky et al. (2003), *J Immunol Methods* 277:141-155). Briefly, approximately 1.5 million dihydrofolate reductase (DHFR) deficient DG44 Chinese hamster ovary (CHO) cells were transfected with 4 μg PV90 plasmid DNA containing the human BCMA gene using Fugene 6 Transfection Reagent (Roche, Indianapolis, Ind.). Following transfection, the cells were cultured in 6-well culture dishes. Twenty-four hours post-transfection, the growth medium was changed to alpha minus MEM (Gibco, Rockville, Md.), 10% dialyzed serum (Hyclone, Logan, Utah), and 2 mM L-glutamine (Gibco, Rockville, Md.), and cells were pooled and split into three T-75 tissue culture flasks and allowed to grow to confluence. Seven days post-transfection, the cells were pooled again and split into five T225 tissue culture flasks and allowed to grow to confluence.

Fourteen days post-transfection, the cells were incubated with the C4E2.2 Ab (6) and sorted for BCMA+ cells. These cells were grown in culture and sorted a second time, with positive cells sorted into 96-well plates. Clones were expanded and assessed for BCMA expression using clone C4E2.2.

Figure 1B:
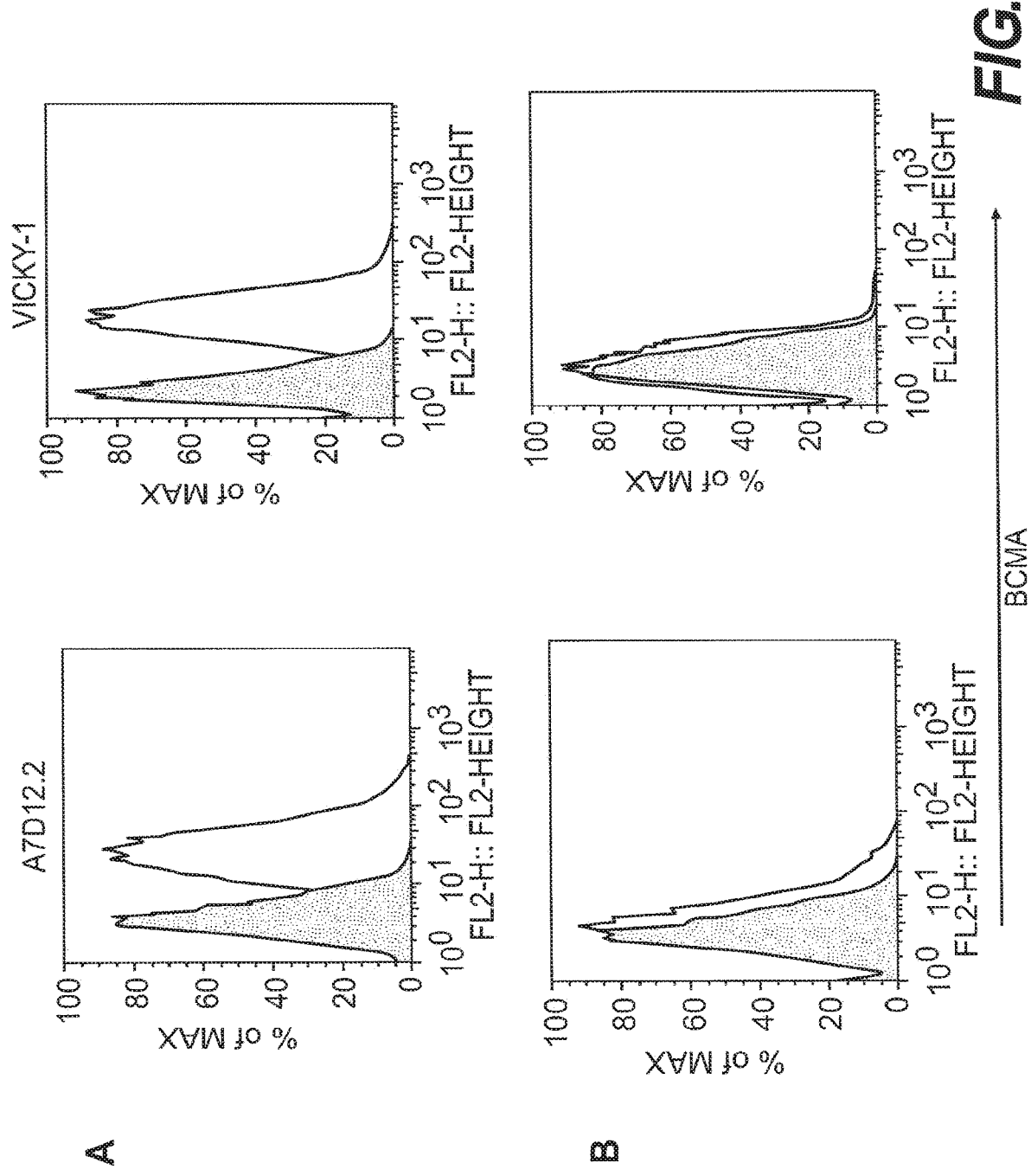
Figure 1C:
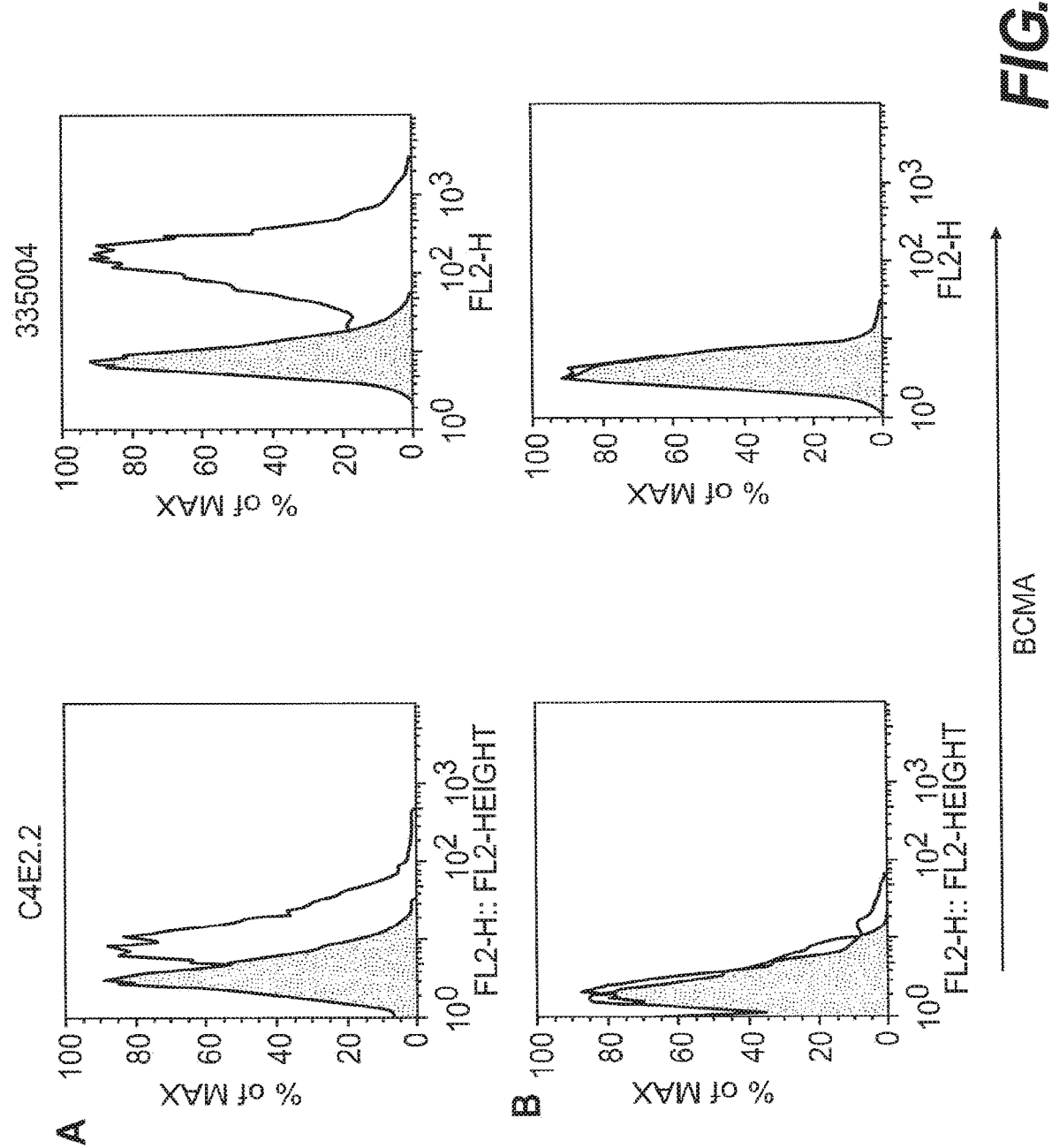

The highest expressing clone was used for assessing new anti-human BCMA mAbs, with untransfected CHO cells as a control. Briefly, BCMA-CHO cells were pretreated with FACS buffer plus 5% normal mouse serum to block non-specific binding sites. Seven anti-BCMA mAbs—C11D5.3, C12A3.2, C13F12.1 and A7D12.2 and the commercially available anti-BCMA mAbs, C4E2.2 (Legacy Biogen), VICKY-1 (Alexis) and 335004 (R&D Systems, Inc.)—and isotype control antibodies were incubated separately with cells for 30 minutes on ice at 1 μg/ml, and washed. Biotin-conjugated isotype control Abs were as follows: mouse IgG1, eBioscience cat. no. 13-4714-85; mouse IgG2a, eBioscience, cat. no. 13-4732-85; hamster IgG1, BD Pharmingen cat. no. 553970; rat IgG2a, eBioscience, cat. No. 13-4321-82. To visualize positive staining, Streptavidin-PE (Molecular Probes, Eugene, Oreg.) was added to cells for 30 minutes on ice, after which cells were washed, fixed in 0.8% paraformaldehyde, and run on a FACScalibur flow cytometer (BDbiosciences, San Jose, Calif.) and analyzed using Flowjo software (Treestar, Ashland, Oreg.). Results are shown in FIG. 1.

All seven antibodies showed specific recognition of the BCMA-expressing cells. C11D5.3 showed a slightly higher basal binding to the negative control cells than the control mAb; basal binding of the other six antibodies to the negative control cells was similar to that of the control Ab.

Example 4. Analysis of Anti-BCMA mAb Epitope Overlap by Cross-Blocking ELISA

The seven anti-BCMA mAbs tested in Example 3 were then assessed in a cross-blocking assay to determine the presence or absence of epitope overlap between each antibody. Corning 96-well flat-bottom plates were incubated overnight at 4° C. with 10 μg/ml of mouse anti-human Fc in a 50 mM pH 9.6 sodium bicarbonate solution, washed, incubated with 2 μg/ml human BCMA-Fc (SEQ ID NO:10) at 37° C. for 1 hr, washed again, and non-specific binding sites were blocked with blocking buffer (3% BSA in PBS) for 30 min at 37° C. Triplicate wells were then incubated with each unconjugated anti-BCMA mAb clone in blocking buffer at a concentration that was ten times the concentration of the single biotin-conjugated anti-BCMA mAb used in each individual experiment. A single biotin-conjugated anti-BCMA mAb clone in blocking buffer was added to all wells at a concentration pre-determined to give 80% of maximal signal (EC80) and incubated for 1 hr at 37° C., after which wells were washed and incubated with a streptavidin-HRP solution for 30 min, 37° C., washed, and incubated with substrate, TMB, to visualize positive reactivity. Enzymatic reactivity was stopped by adding 2N sulfuric acid, and the absorbance at 450 nm was measured using a plate reader.

For each species of biotin-conjugated antibody, control readings in which the unconjugated and conjugated antibodies were the same (except for the presence/absence of conjugated biotin) were considered background levels, i.e., the absorbance from this control was subtracted from each experimental reading for that antibody. In some cases, this background subtraction resulted in slightly negative values. Although it is possible that the labeled antibody was blocked slightly more effectively by a different unconjugated antibody than by itself, these slightly negative values might also result from experimental variation. Results were then expressed as a percentage of the positive control value, i.e., the background-adjusted absorbance reading for the biotin-conjugated antibody in the absence of a competing unconjugated antibody.

Antibodies were considered to bind the same epitope or very closely overlapping epitopes if they each reduced the other's binding (according to the fraction calculated as above) to below 20% of the positive control value. If they did not satisfy this condition, they were considered to have at least partially distinct epitopes. Table 3 shows which antibodies have at least partially distinct epitopes.

Example 5. Flow Cytometric Analysis of Antibody Binding to Human Peripheral Blood Cells Blood was obtained from consenting healthy volunteers and peripheral blood mononuclear cells (PBMCs) were enriched by centrifugation through Ficoll-Paque (GE Healthcare, UK) according to the manufacturer's recommendations. PBMCs were washed extensively in PBS prior to use. Cells were pretreated with FACS buffer containing 5% normal mouse serum to block non-specific binding sites. The following fluorphore-conjugated monoclonal antibodies directed against specific B cell and plasma cell markers were used: anti-CD19-PE-Cy5, anti-IgD-FITC, anti-CD27-APC, anti-CD38-PE-Cy7 (BD Biosciences, San Jose, Calif.). Streptavidin-PE (Molecular Probes, Eugene, Oreg.) was used to visualize biotin-conjugated anti-BCMA mAbs (10 μg/ml). Binding of an isotype control mAb as in Example 3 was also measured.

Figure 2A:
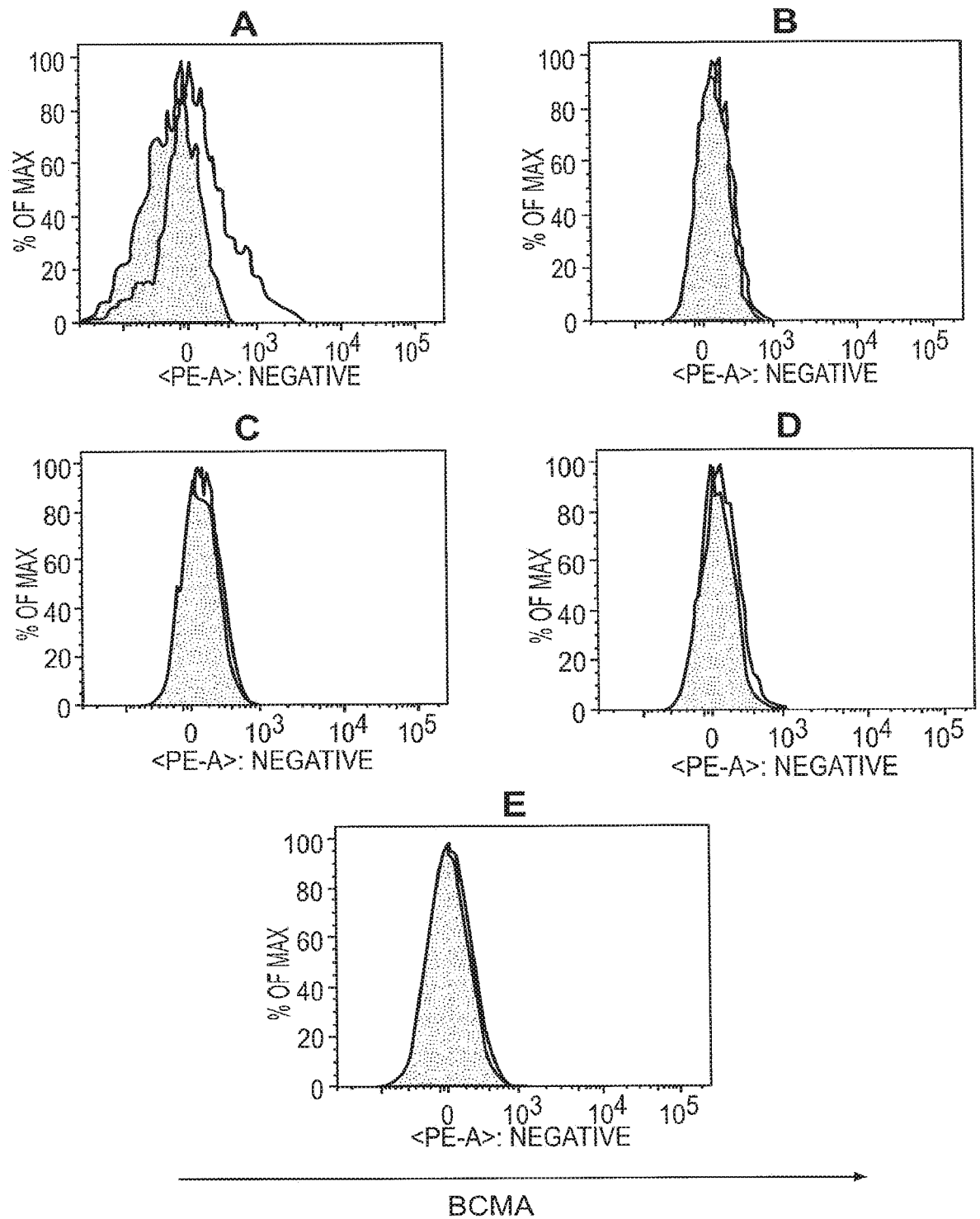
FIGS. 2A-2F depict anti-BCMA binding to B cell subsets. B cell subsets in human peripheral blood were assessed by flow cytometry for reactivity to anti-BCMA mAbs. Visualization was as in FIG. 1. The shaded area represents staining with an isotype control Ab. B cell subsets were plasma cells (CD19$^+$CD27$^{high}$CD38$^{high}$gD$^-$) (FIG. 2A), switched memory B cells (CD19$^+$CD27$^{high}$CD38$^{low}$ IgD$^-$) (FIG. 2B), unswitched memory B cells (CD19$^+$CD27$^{high}$CD38$^{low}$ IgD$^+$) (FIG. 2C), double negative memory B cells (CD19$^+$CD27$^-$CD38$^{low}$ IgD$^-$) (FIG. 2D), and naïve B cells (CD19$^+$CD27$^-$ IgD$^+$) (FIG. 2E).
Figure 2B:
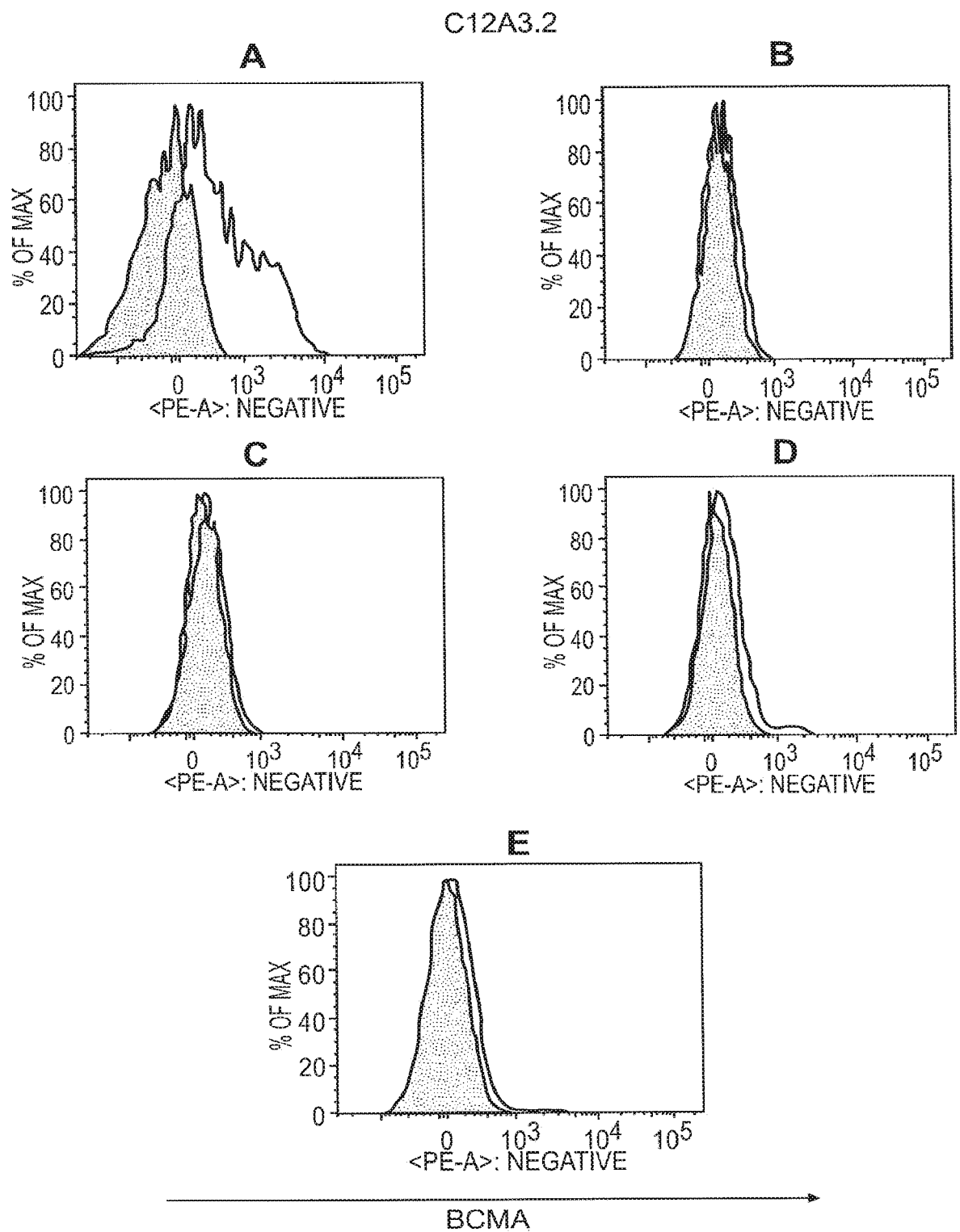
Figure 2C:
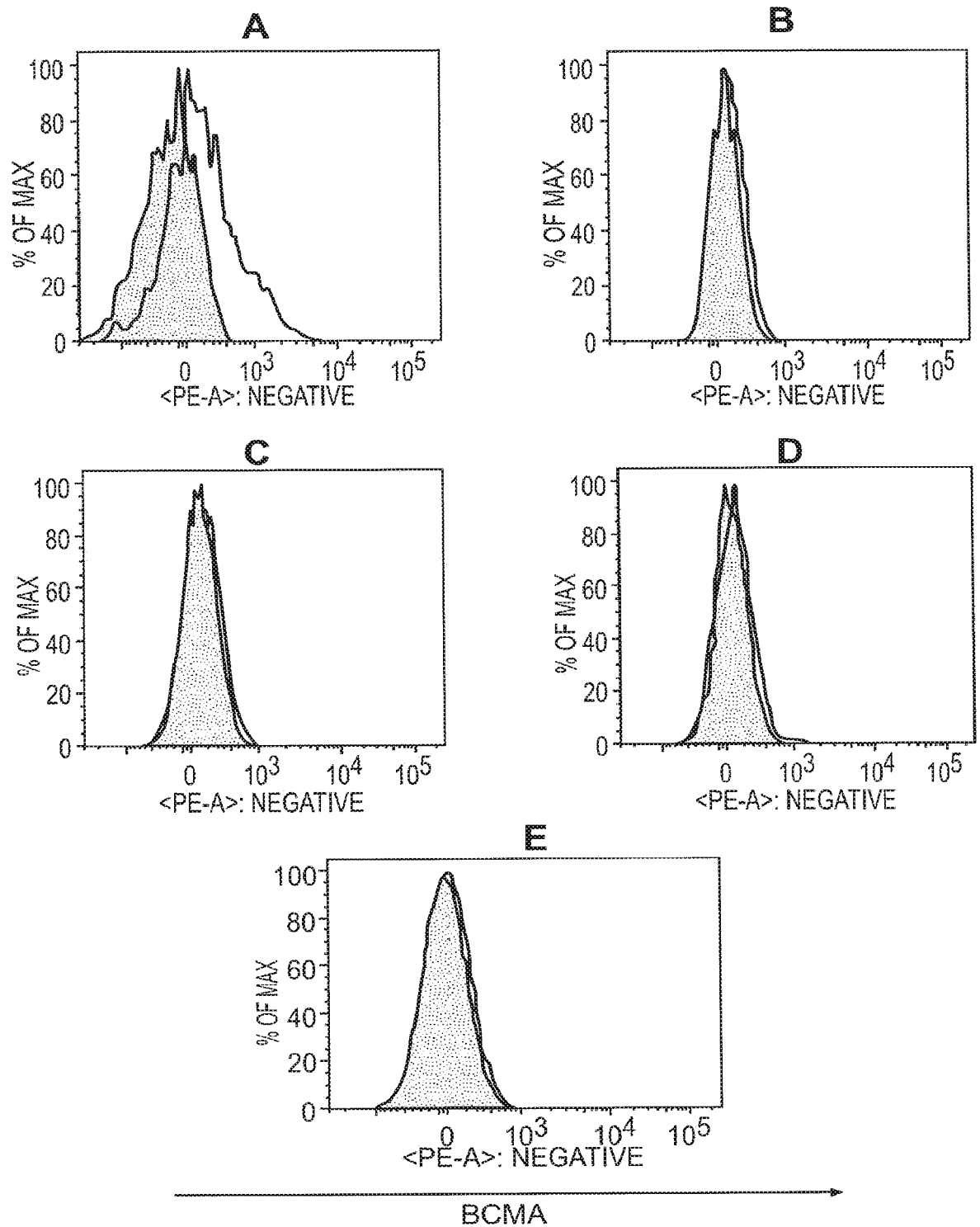
Figure 2D:
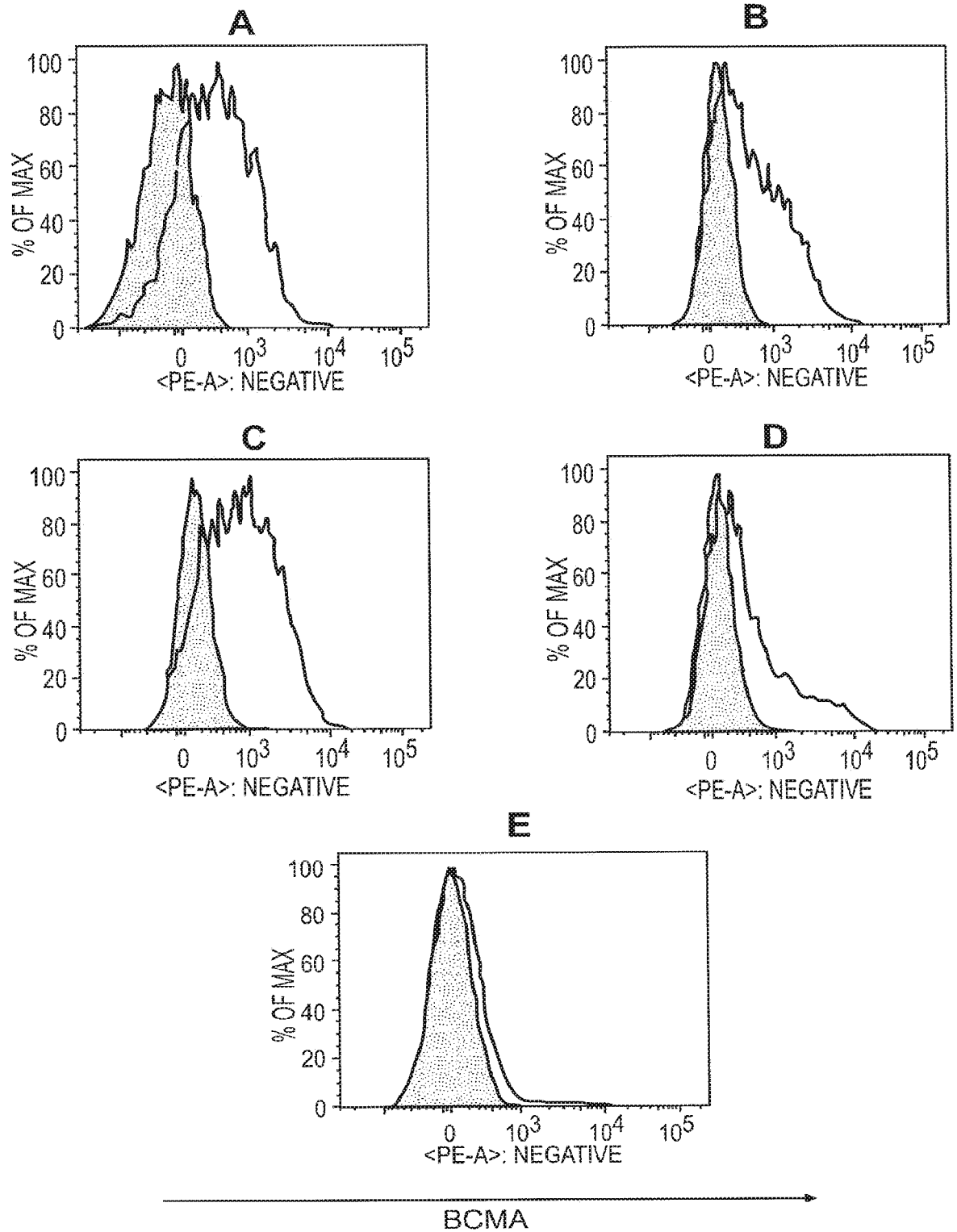
Figure 2E:
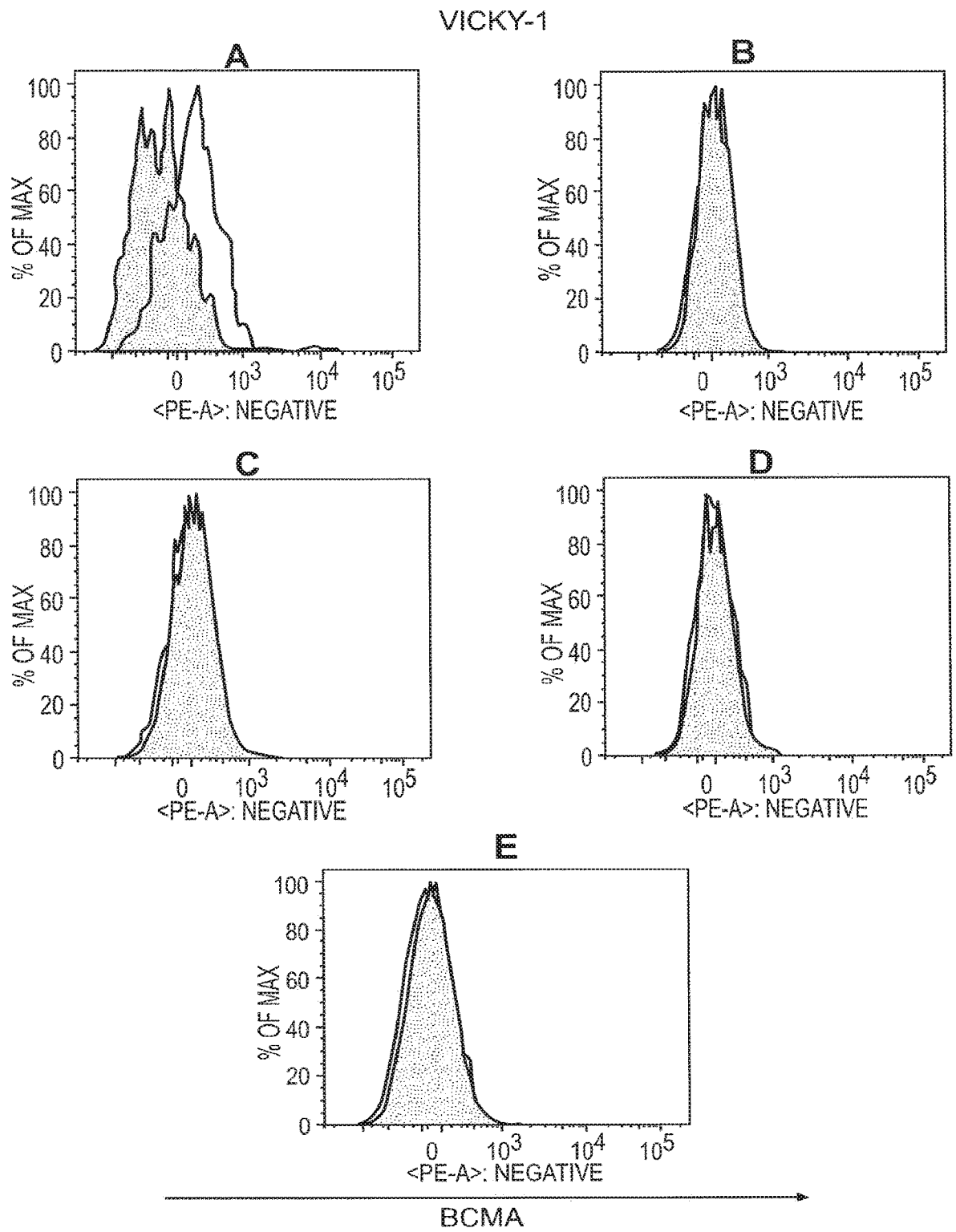
Figure 2F:
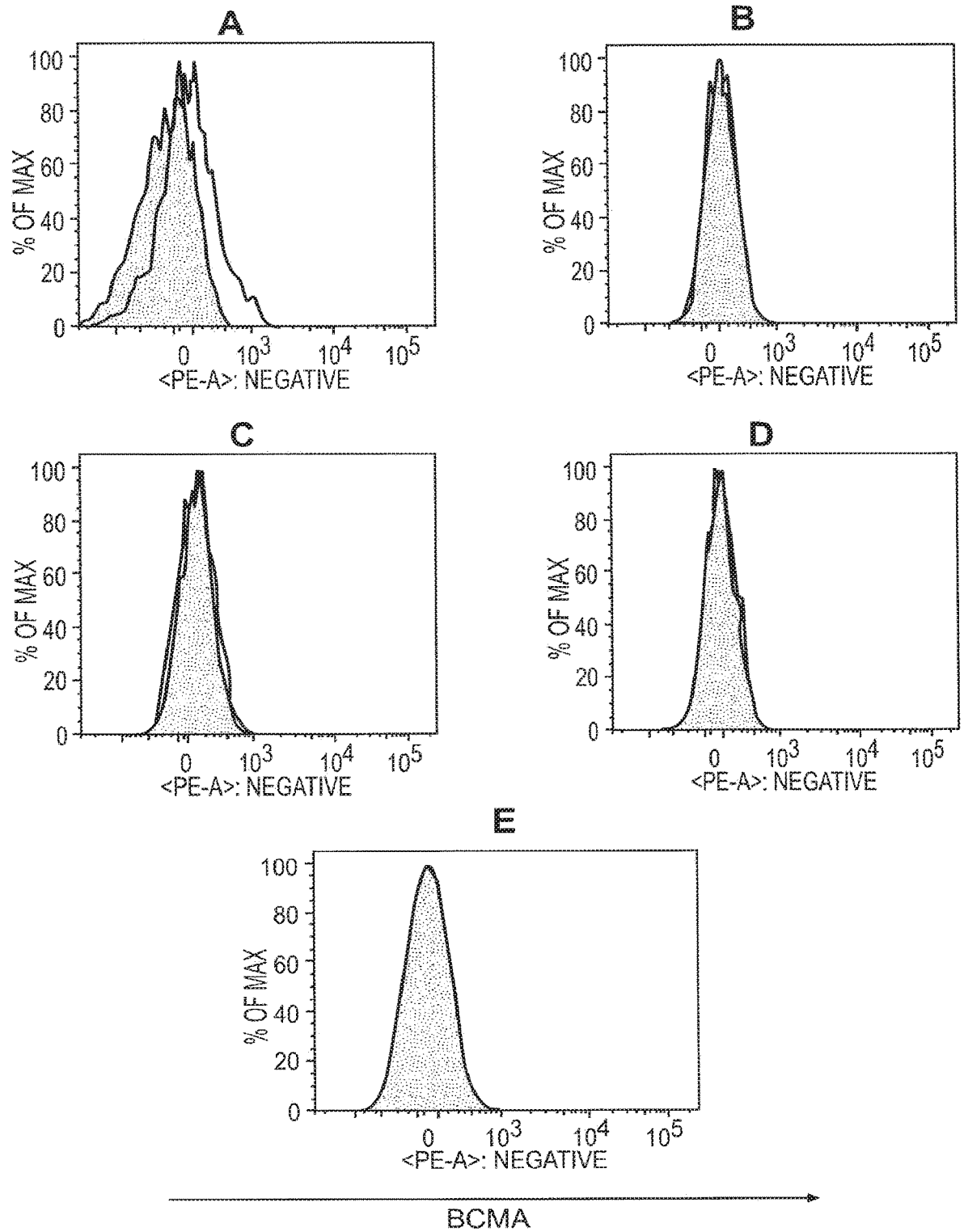

None of the anti-BCMA mAbs stained naïve B cells from healthy volunteers (FIG. 2E), while all stained plasma cells, although with varying intensities (FIG. 2A). Only clone A7D12.2 stained a proportion of all three memory B cell subsets (FIGS. 2B-D).

Figure 3A:
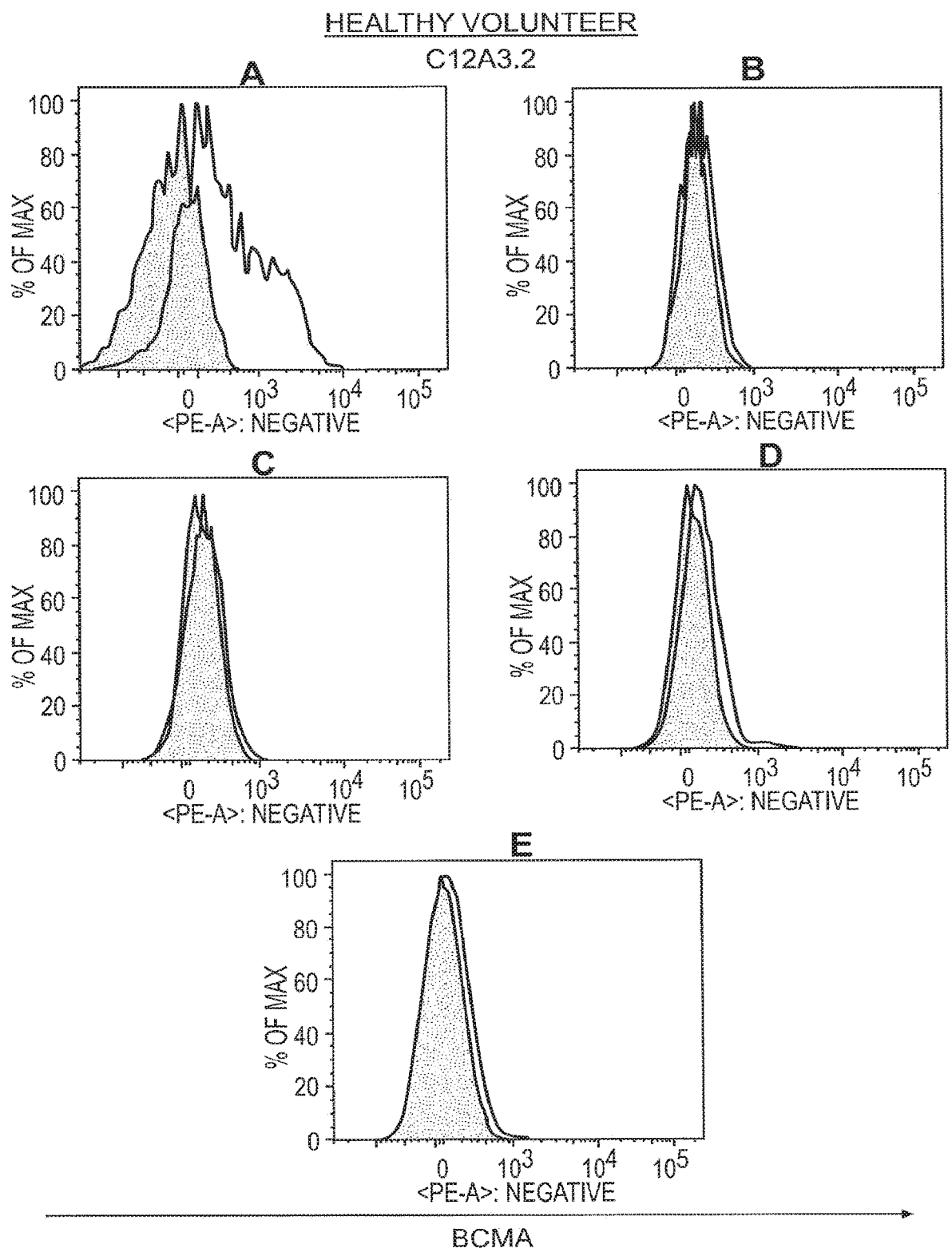
FIGS. 3A-3D depict anti-BCMA binding to B cell subsets isolated from healthy and SLE-afflicted individuals. B cell subsets in human peripheral blood from a healthy volunteer and an SLE patient were assessed by flow cytometry for reactivity to the anti-BCMA mAbs C12A3.2 and A7D12.2. B cell subsets were as in FIG. 2. Visualization was as in FIG. 1.
Figure 3B:
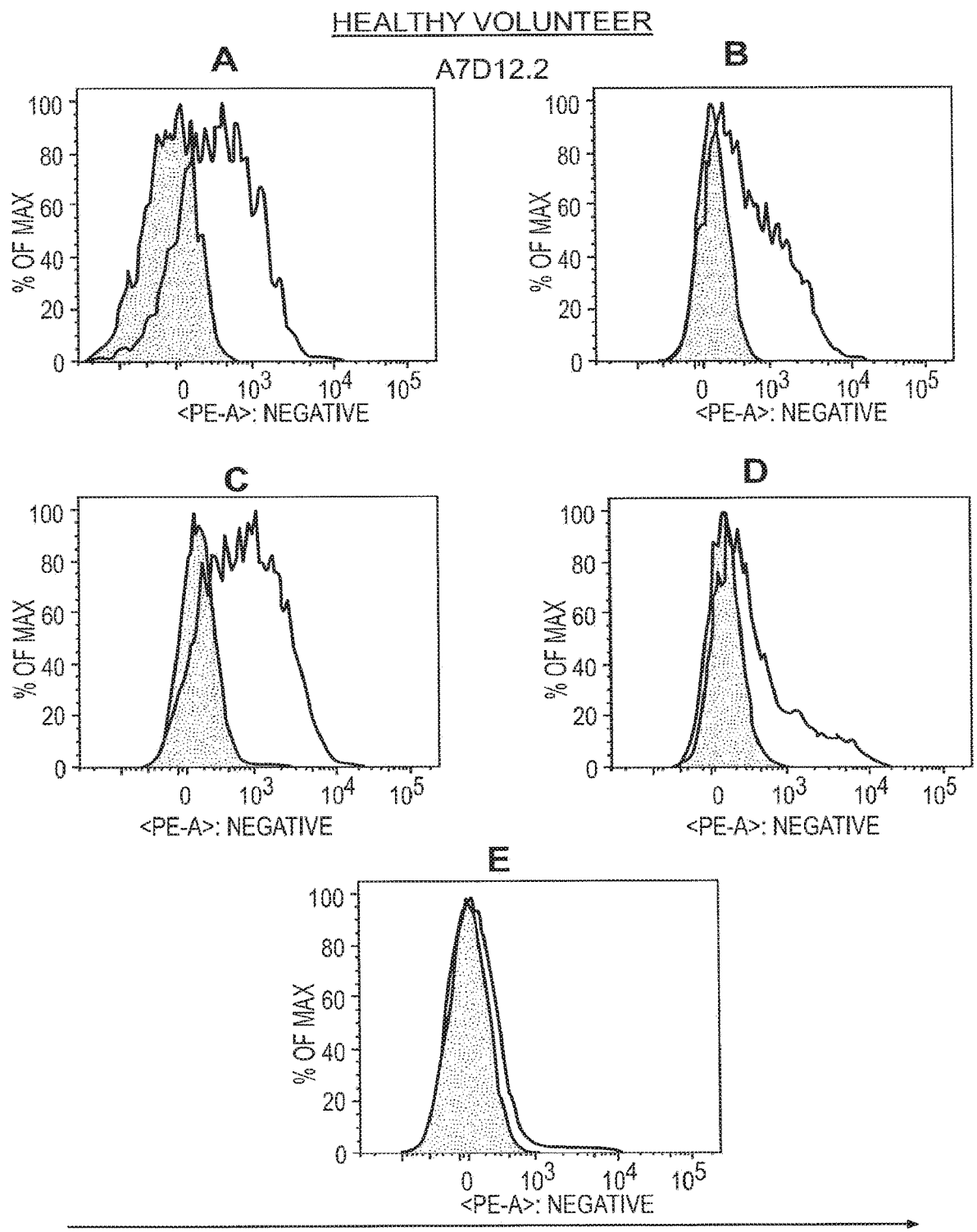
Figure 3C:
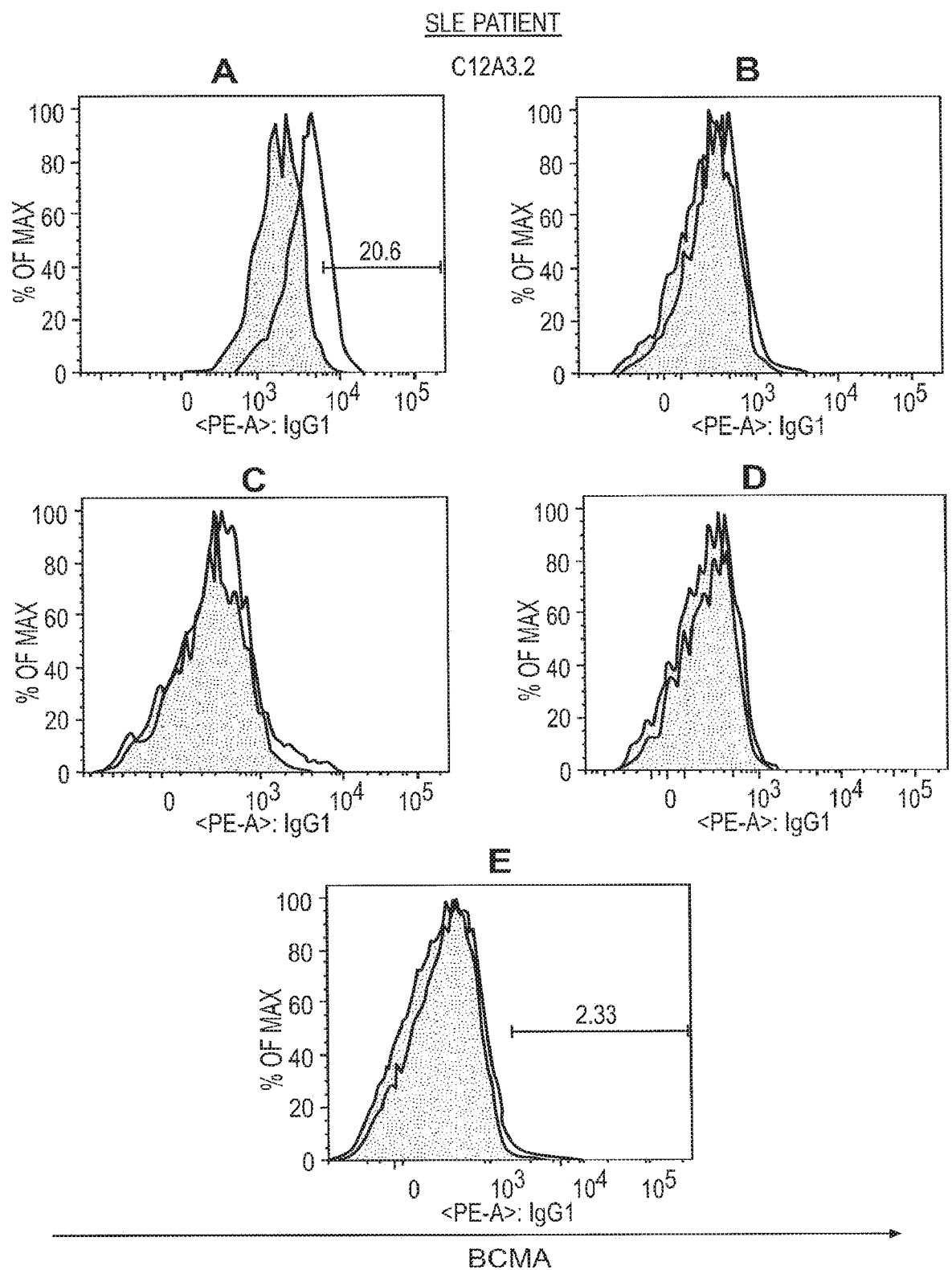
Figure 3D:
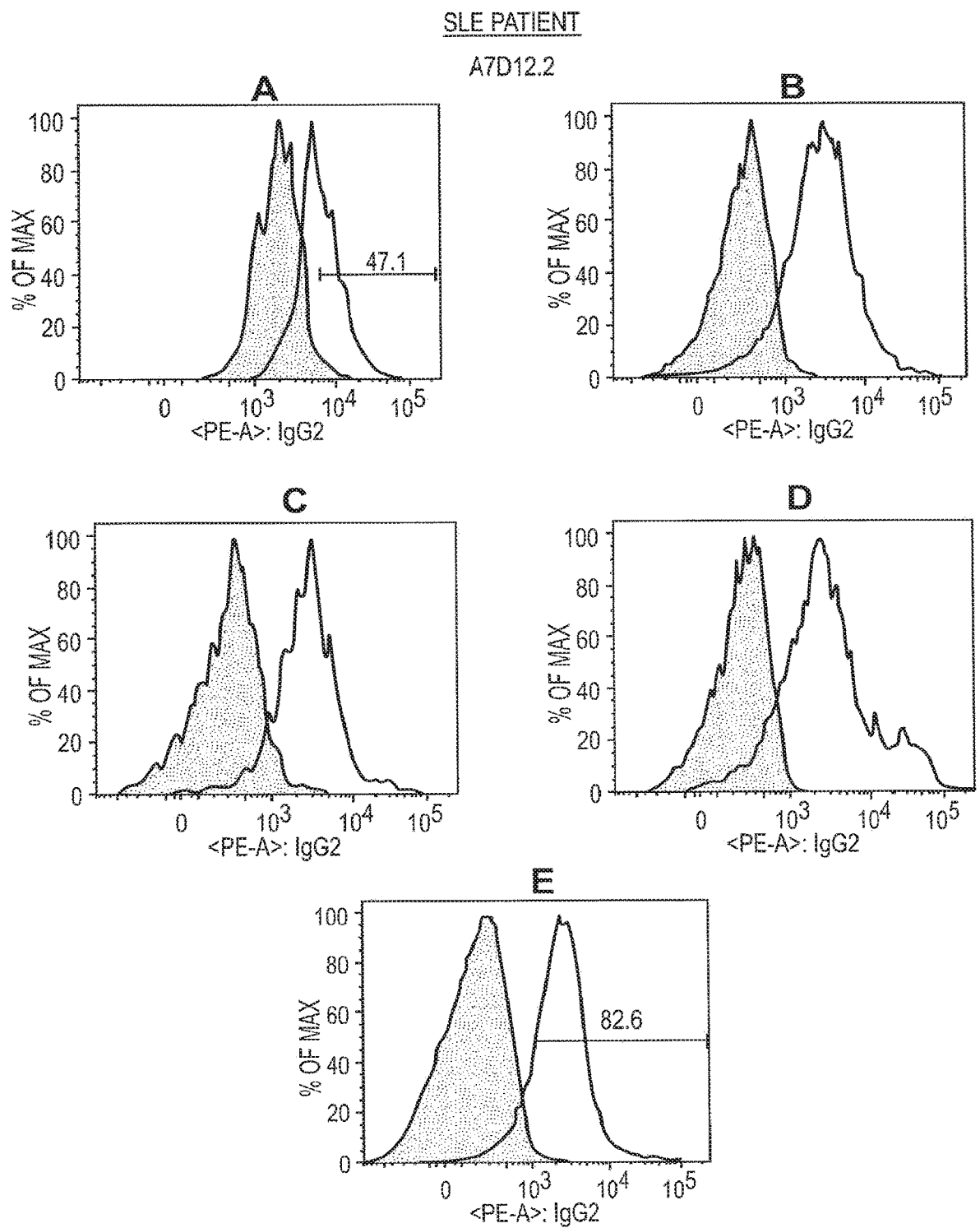

Example 6. Comparison of Antibody Binding to B Cells of Healthy and SLE-Afflicted Individuals Blood was obtained from consenting healthy volunteers and SLE patients and processed as in Example 5. FIGS. 3A-D show a comparison between samples from a healthy volunteer and a representative SLE patient. Antibody A7D12.2 bound to plasma cells from both healthy volunteers and SLE patients (FIG. 3A). In the SLE samples but not the healthy samples, the A7D12.2 antibody bound naïve B cells (FIG. 3E). Binding of the A7D12.2 antibody to memory B cells (FIGS. 3B-3D), particularly double negative memory B cells (FIG. 3D), was increased in SLE samples.

Example 7. Generation of Cell Lines Producing Chimeric Anti-BCMA mAbs

CHO-DG44-I, a dhfr-deficient, insulin-independent Chinese hamster ovary cell line, was used to construct anti-BCMA wild type cell lines. The host cells were cultured in CHO-S-SFM II medium with nucleosides prior to transfection.

Chimeric antibodies were produced by transfecting cells with expression plasmids encoding the mature heavy and light chain sequences listed in Table 4.

TABLE 4

Mature heavy and light chain sequences of chimeric anti-BCMA antibodies

| Chimeric antibody | Mature heavy chain sequence | Mature light chain sequence |
| --- | --- | --- |
| chA7D12.2 | SEQ ID NO: 13 | SEQ ID NO: 14 |
| chC11D5.3 | SEQ ID NO: 15 | SEQ ID NO: 16 (for Example 8) SEQ ID NO: 17 (for Example 9) |
| chC12A3.2 | SEQ ID NO: 18 | SEQ ID NO: 19 |
| chC13F12.1 | SEQ ID NO: 20 | SEQ ID NO: 20 |

Chimeric anti-BCMA expression plasmids were transfected into the CHO host cell line DG44-I using a cationic lipid (Fugene HD) method. Briefly, 1×10$^6$ DG44-I cells were seeded in each of two wells of a 6-well plate containing 3 mL of CHO-S-SFMII medium w/nucleosides per well. Four μg of plasmid DNA (2 μg heavy chain, 2 μg light chain) was diluted into 200 μL CHO-S-SFM II (Invitrogen) medium at room temperature. Sixteen μL of Fugene HD (Roche) reagent and allowed to complex with the DNA for approximately 15 minutes. 100 μL of the complexed DNA mixture was added to each well containing the cells. After three days, the transfected cells were combined and transferred to a T-75 flask containing 20 mL CHO-S-SFM II medium w/o nucleosides containing 400 μg/mL geneticin (Invitrogen). Cells were monitored for viability and scaled-up accordingly. As the cells were scaled-up they were adapted to production medium. Clonal cell lines were obtained by FACS sorting individual cells from the stable population.

CHO-DG44-I cells stably transfected with chimeric heavy and light chains were fermented in CHOM39 media, harvested, and the cells were removed by centrifugation. The pH of the cleared media was adjusted prior to passing through a protein A Fast Flow column. Antibodies were eluted with 100 mM Na-citrate buffer, pH 3.0, neutralized to pH 7.0 using 10% (v/v) of 2M glycine, pH 8.9, and the recovered antibody solution was buffer-exchanged to PBS (pH 7.2) using a Superdex 200 size exclusion chromatography under endotoxin-free conditions. The purified protein was kept at −80° C.

Example 8. Anti-BCMA-Mediated Killing In Vitro

Cells and Cell Culture

JJN-3 human plasmacytoma cells (DSMZ ACC 541) were cultured in culture medium consisting of 40% Dulbecco's MEM, 40% Iscove's MDM, 20% FBS, 100 units/mL penicillin and 100 μg/mL streptomycin. U266 human plasmacytoma cells (ATCC TIB 196) were cultured in culture medium consisting of RPMI 1640, 15% FBS, 20 mM HEPES, 100 units/mL penicillin and 100 μg/mL streptomycin. All cells were cultured at 37° C. in a 5% CO2 atmosphere. Peripheral blood mononuclear cells were isolated from a consented normal healthy donor by density centrifugation through Ficoll-Paque PLUS (GE Healthcare, Uppsala, Sweden).

In Vitro Antibody-Dependent Cellular Cytotoxicity (ADCC) Assay

Assay diluent was RPMI 1640, 1% BSA, 20 mM HEPES, 100 units/mL penicillin and 100 μg/mL streptomycin. Human plasmacytoma cell lines JJN-3 and U266 were washed and resuspended in assay diluent to $0.4 \times 10^6$ cells per mL. 50 μL of each cell suspension was plated into a 96-well U bottom microtiter plate in triplicates. 50 μL of serially diluted chimeric anti-BCMA antibodies (chC12A3.2, chC13F12.1, chC11D5.3, and chA7D12.2, as described in Example 7) and control human IgG1 (HIgG1; Protos Immunoresearch, Burlingame, Calif.) were added to wells containing the cell lines and incubated for 30 minutes at 37° C. For an effector:target ratio of 25:1, 50 μL of PBMCs (500,000) were added and incubated for an additional four hours at 37° C. in a 5% CO2 atmosphere. Plates were centrifuged at 1200 rpm for 5 minutes, and 100 μL of supernatant was transferred to a 96-flat-bottom microwell plate. The level of cell lysis was determined by measuring the amount of lactate dehydrogenase (Cytotoxicity Detection Kit (LDH), #11 644 793 001 Roche) released from lysed cells. 100 μL of LDH kit reaction mixture was added to 100 μL of supernatant for up to 30 minutes as followed by manufacturer instructions. Absorbance was measured at 490 nm. Controls included target cells alone (spontaneous LDH release), target cells alone with 2% Triton X-100 in assay diluent (maximum LDH release), effector cells with and without target cells, and human IgG1 isotype control.

Results

The human BCMA+ plasmacytoma cell line, U266, was utilized to test the ability of chimeric anti-BCMA antibodies to kill via ADCC. Human peripheral blood mononuclear cells (PBMCs) were used as effector cells. As shown in Table 5, chimeric mAbs C12A3.2 and C13F12.1 demonstrated marked ADCC activity relative to HIgG1 controls. Chimeric clones A7D12.2 and C11D5.3 also mediated ADCC, although to a lesser degree than C12A3.2 and C13F12.1.

TABLE 5

ADCC of U266 cells by anti-human BCMA mAbs

| mAb Clone | % Killing at 1 nM | % Maximal Killing (mAb concentration, nM) |
|---|---|---|
| chC12A3.2 | 32 | 35 (4) |
| chC13F12.1 | 20 | 20 (0.4) |
| chA7D12.2 | 10 | 24 (100) |
| chC11D5.3 | 18 | ≥42 (≥100)[1] |

[1]Maximum killing determination is incomplete

ADCC assays were also performed using a second BCMA+ plasmacytoma cell line, JJN-3, as the target cells. As shown in Table 6, chimeric C12A3.2, C13F12.1, and A7D12.2 also mediated ADCC of JJN-3 cells.

TABLE 6

ADCC of JJN-3 cells by anti-human BCMA mAbs

| mAb Clone | % Killing at 1 nM | % Maximal Killing (mAb concentration, nM) |
|---|---|---|
| chC12A3.2 | 5 | 14 (100) |
| chC13F12.1 | 3 | ≥14 (≥100)[1] |
| chA7D12.2 | 20 | 37 (100) |

[1]Maximum killing determination is incomplete

Using enriched human NK cells as effector cells did not result in improved killing for chC12A3.2, chC13F12.1 or chA7D12.2. Rather, percent killing by NKs was diminished relative to PBMCs, indicating that NK cells are not the effector cells for chC12A3.2, chC13F12.1, or chA7D12.2 in the ADCC assays with U266 and JJN3 as target cells (data not shown). Generation of afucosyl variants of chC12A3.2, chC13F12.1, or chA7D12.2 did not improve activity of these mAbs (data not shown).

Example 9. Anti-BCMA-Mediated Cell Depletion In Vivo

Establishment of Humanized (HSC/NSG) Mice

HSC/NSG mice provide a useful tool for testing in vivo biologic reagents specific for human protein targets since their immune system consists of functioning human cell types (Brehm et al. (2010), Clin Immunol [Epub ahead of print]). Humanized mice were generated as previously described (Pearson et al. (2008), Curr Protoc Immunol Chapter 15:Unit 15.21.PMID: 18491294). NOD/SCID/common gamma chain-deficient mice (NSG mice) were purchased from Jackson Laboratories (Bar Harbor, Me.). Mice were maintained and bred under specific-pathogen-free conditions in isolator cages. Breeding pairs were established and dams were monitored for pregnancy and delivery. Pups ranging in age from 2-6 days old were used to create humanized mice. Pups were lightly irradiated, receiving a dose of 1 Gy (100 rad) from a 137Cs irradiator. Pups were immediately injected intra-orbitally with approximately 50,000 CD34+CD3-human stem cells (HSC) derived from umbilical cord blood (All Cell LLC, purchased from StemCell Technologies Inc., Vancouver, BC, Canada), then returned to the dam. Pups were weaned at 21 days and caged with littermates according to gender. Starting at 3 months of age mice were bled via the facial vein into heparinized tubes and the whole blood was analyzed by flow cytometry for the presence of human cells. In brief, 100 μl whole blood was stained with a cocktail of mAbs, anti-human CD45-FITC, anti-human CD3-PE, anti-human CD19-PerCp, and anti-mouse CD45-APC (BD Biosciences, San Jose, Calif.). Mice were considered successfully humanized if they had at least 20% human CD45+ cells in whole blood of which 10% or more were human CD3+, the remainder being human B cells and other human hematopoietic cells. Mice were occasionally bled and analyzed to ensure that the humanization was stable, and were routinely analyzed 2 weeks prior to study enrollment.

Flow Cytometry

To identify plasma cells (PC) in human stem cell humanized NSG (HSC/NSG) mice, collagenase-digested spleens were subjected to flow cytometric analysis. Cells were incubated with a cocktail of mAbs directed to human cell lineage and to human B cell markers. The panel consisted of anti-human CD45, anti-human CD19, anti-human CD27, anti-human IgD, and anti-human CD38. Two markers used to exclude specific cell populations were anti-mouse CD45 and anti-human CD3. Cells identified as PC were human CD45+, human CD19+, human CD3-, human CD27+, human IgD- and human CD38bright. To identify BCMA+ cells the biotin-conjugated anti-human BCMA mAbs, C12A3.2 and A7D12.2, were used.

In Vivo Cell Depletion Assay 5-6 month-old HSC/NSG mice received chimeric anti-BCMA mAb i.p. Human IgG1 with no known reactivity (Protos Immunoresearch) was used as a negative control. Blood was collected to prepare serum for analysis of human Ig isoform levels. At the study terminus the spleen was harvested, a single cell suspension was prepared, RBCs were lysed and cells were washed 3× with PBS/5% FCS and the cell number was determined. Cells were assessed by flow cytometry for T lineage cells, B lineage cells, and plasma cells.

Assessment of Serum Human Ig Isotypes

Serum levels of human IgM and IgG were determined using an ELISA format (Bethyl Laboratories Inc., Montgomery, Tex.) and a human immunoglobulin isotyping kit (Millipore, Billerica, Mass.), respectively, according to the manufacturer's protocol.

Results

Figure 4:
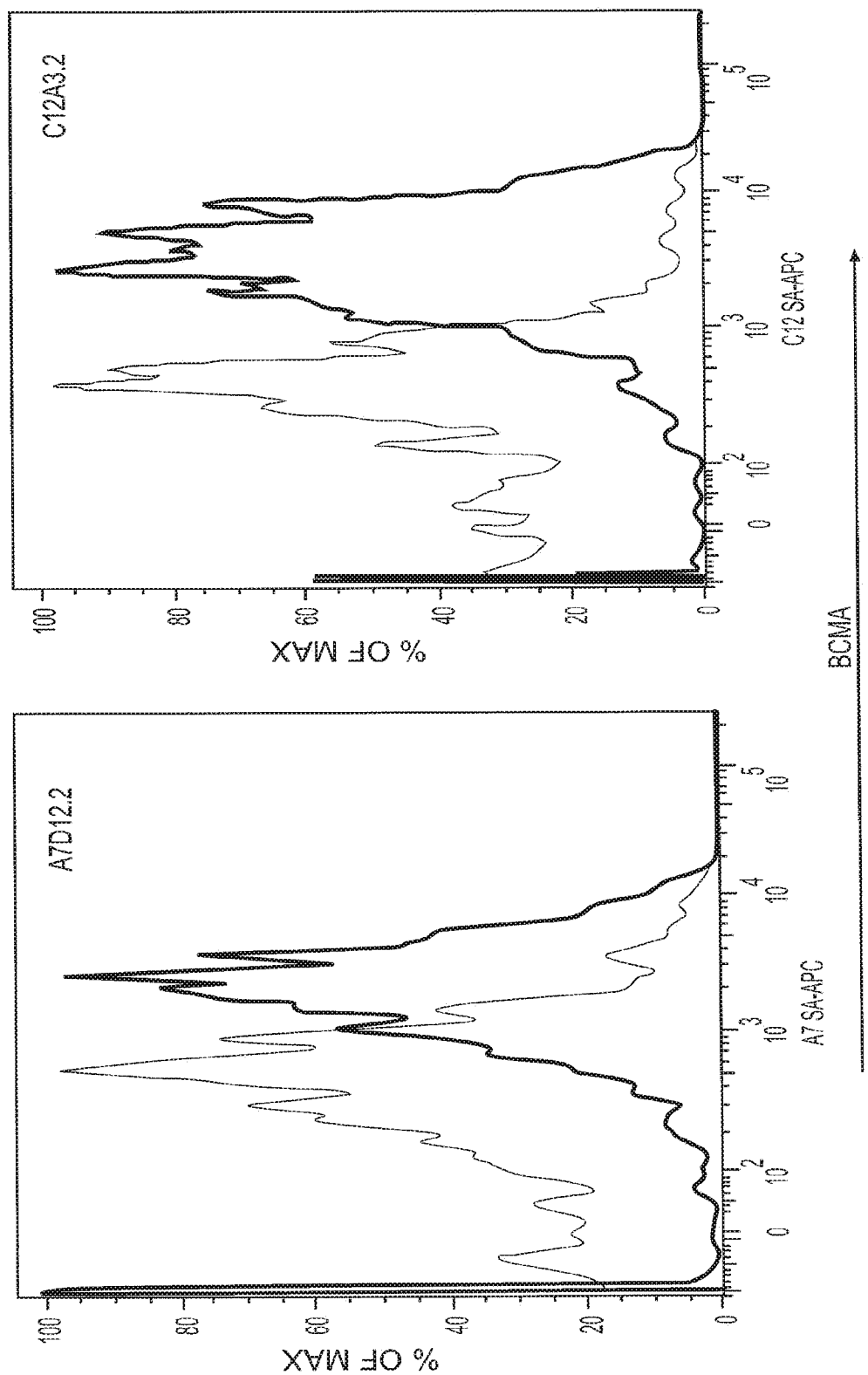
FIG. 4 depicts flow cytometric staining of human plasma cells within the human CD45$^+$ splenocyte compartment isolated from HSC/NSG mice. Splenic plasma cells were stained with anti-BCMA antibodies A7D12.2 (left panel; bold line) and C12A3.2 (right panel; bold line) or an isotype control mouse IgG2b or IgG1 Ab, respectively (thin line in both panels).

Analysis of HSC/NSG mice aged 5-6 months revealed that among the diverse cell subsets assessed BCMA+ cells were only found in the B cell lineage. Within the B cell lineage, BCMA was found only on splenic PCs (human CD19+, human CD27+, IgD-, CD38 bright) (FIG. 4), and not on naïve B cells (human CD19+, human CD27-, IgD+), unswitched memory B cells (human CD19+, human CD27+, human IgD+), or switched memory B cells (human CD19+, human CD27+, human IgD-) (data not shown).

To assess the ability of chimeric anti-human BCMA mAbs to deplete human PC, HSC/NSG mice received various amounts of chimeric anti-human BCMA clones chAC11D5.3, chC12A3.2, chC13F12.1, and chA7D12.2 (Example 7) twice weekly i.p. for 2 weeks, after which the presence of splenic PCs was determined. Splenic PCs from the HIgG1-treated control group were analyzed for expression of BCMA using the A7D12.2 and C12A3.2 clones and were confirmed to express cell surface BCMA (data not shown). PCs were identified using the flow cytometric parameters described above, and total cell numbers were determined from the flow cytometric dot plots (calculated as a percentage of the total human cell number). The numbers of naïve human B cells, unswitched memory human B cells, and switched memory human B cells were also determined.

Figure 5:
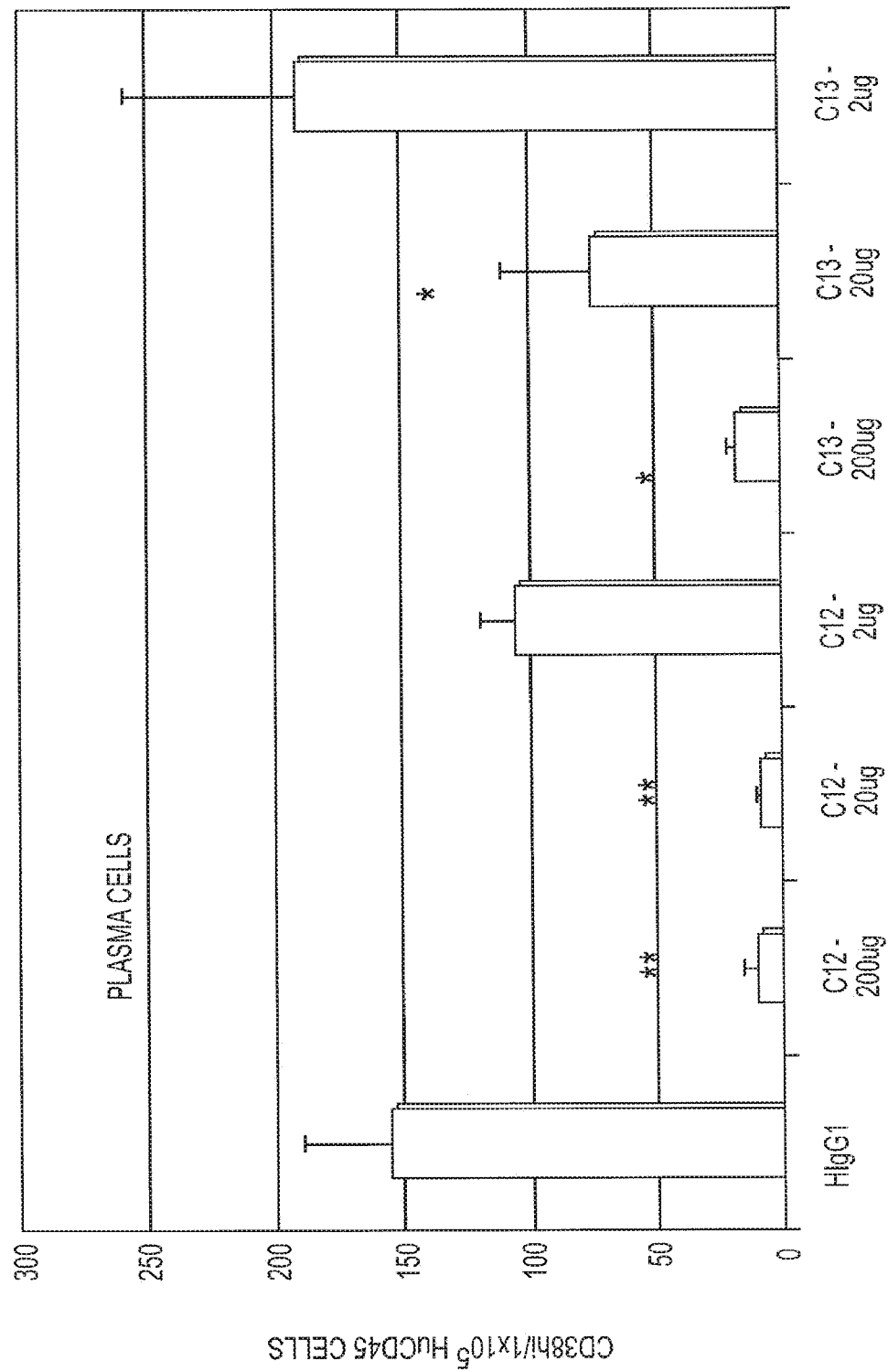
FIG. 5 depicts flow cytometric staining for plasma cells (PCs) within the human CD45$^+$ splenocyte compartment isolated from HSC/NSG mice treated with anti-BCMA antibody (chC12A3.2 or chC13F12.1) or human IgG1 control. Mice were injected i.p. with anti-BCMA Ab or HIgG1 control twice weekly for 2 weeks. ** p<0.0001; * p=0.0066.

Treatment with chC12A3.2 (N=5) resulted in a statistically significant decline, 93% and 95%, in the number of splenic PCs at the 200 μg and 20 μg dose levels, respectively, when compared with control HIgG-treated mice (N=5) while the 2 μg dose also showed a marked decline (32%), although it was not statistically significant. Treatment with chC13F12.1 (N=5) resulted in a statistically significant decline, 88% and 51%, in the number of splenic PCs at the 200 μg and 20 μg dose levels, respectively (FIG. 5). No impact on the number of other B cell subsets or T cells was observed with chC12A3.2 and chC13F12.1 (data not shown).

Figure 6:
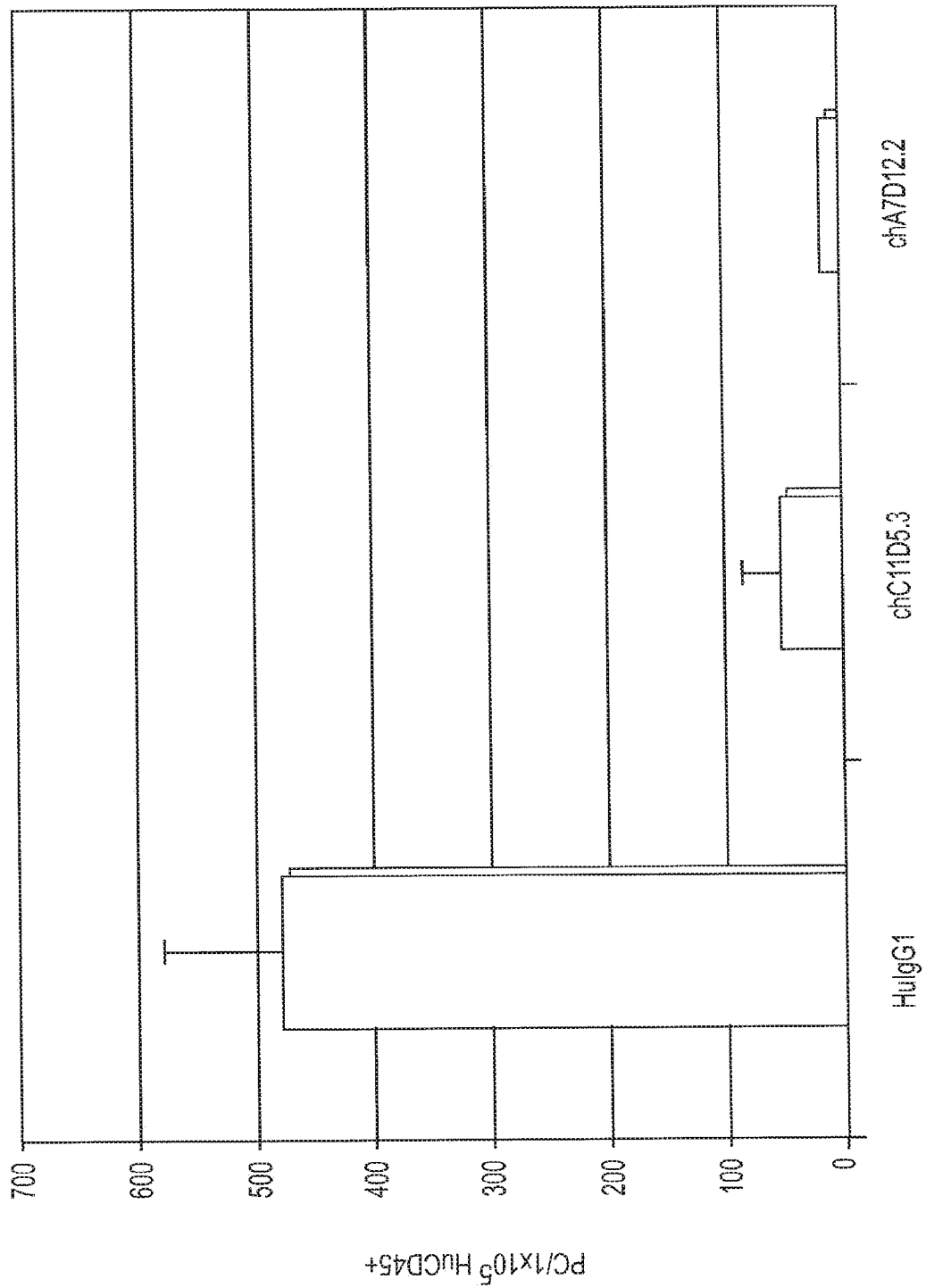
FIG. 6 depicts flow cytometric staining for plasma cells (PCs) within the human CD45$^+$ splenocyte compartment isolated from HSC/NSG mice treated with anti-BCMA antibody (chC11D5.1 or chA7D12.2) or human IgG1 control. Mice were injected i.p. with anti-BCMA Ab or HIgG1 control twice weekly for 2 weeks.

Treatment with 200 μg of chC11D5.1 (N=2) or chA7D12.2 (N=1) resulted in an 89% and 97% reduction, respectively, in human PCs within the spleen when compared to HIgG-treated control mice (N=5) (FIG. 6). Treatment with chA7D12.1 also resulted in a 2.6-fold decline in the number of splenic human switched memory B cells when compared to HIgG-treated mice (575 vs. 217 PCs/$10^5$ HuCD45$^+$ cells, for HIgG and chA7D12.1, respectively). Although BCMA could not be detected on the surface of switched memory B cells in untreated humanized mice, it appears that while the level of BCMA was below the limit of detection by flow cytometry, it was sufficient to result in Ab-mediated killing.

To determine the impact of human PC depletion on serum human Ig levels in the HSC/NSG mice described above, human Ig subsets were analyzed. The chimeric anti-BCMA mAbs used in these studies were of the human IgG1 isoform, therefore human IgG1 levels could not be accurately evaluated. In some experimental cohorts, control-treated mice had very little and variable amounts of isotypes IgG1, IgG2, IgA and IgE (data not shown). As shown in Table 7, both chC12A3.2 and chC13F12.1 resulted in marked reductions in serum human IgM, especially at the higher dose levels. Chimeric C12A3.2 resulted in a 63%, 62% and 30% reduction in IgM for the 200, 20 and 2 μg dose levels, respectively. Chimeric C13F12.1 resulted in a 52%, 42% and 32% reduction in IgM for the 200, 20 and 2 μg dose levels, respectively.

TABLE 7

| | Serum human IgM levels (μg/mL) | | | | | |
|---|---|---|---|---|---|---|
| | Treatment | | | | | |
| Treatment dose | chC12A3.2 | | chC13F12.1 | | Human IgG1 | |
| (μg) | Mean | SD[1] | Mean | SD | Mean | SD |
| 200 | 70.2[2] | 37.4 | 91.1[3] | 26.5 | 190.6 | 67.3 |
| 20 | 73.0[2] | 32.2 | 110.3[4] | 47.3 | ND[5] | |
| 2 | 134.3 | 60.1 | 128.9 | 112.4 | ND | |

[1]SD = standard deviation;
[2]p = 0.008;
[3]p = 0.02;
[4]p = 0.05;
[5]ND = not done In a separate experiment, mice received chC12A3.2 (N=14) or HIgG1 control (N=9), and the control mice had readily detectable IgG2 and IgG3 isotypes as well as IgM. Chimeric C12A3.2-treated mice exhibited a significant depletion of splenic plasma cells, similar to that seen in FIG. 5 (data not shown). As shown in Table 8, mice that received chC12A3.2 exhibited significantly reduced serum IgG2 and IgM levels when compared with HIgG-treated control mice. Chimeric C12A3.2-treated mice also had a marked reduction in serum IgG3, although the difference did not reach statistical significance when compared to control mice (Table 8).

TABLE 8

Serum human immunoglobulin levels

| Treatment | Serum Immunoglobulin (μg/mL) | | | | | |
|---|---|---|---|---|---|---|
| | IgG2 | | IgG3 | | IgM | |
| | Mean | SE[1] | Mean | SE | Mean | SE |
| chC12A3.2 | 5.4[2] | 1.9 | 1.1 | 0.7 | 40.5[3] | 12.2 |
| HIgG | 19.2 | 7.6 | 6.9 | 4.1 | 114.3 | 19.1 |

[1] SE = standard error;
[2] p = 0.05;
[3] p = 0.003

The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polypeptide comprising an antigen binding fragment of an antibody that binds to the polypeptide of SEQ ID NO:9, wherein the antigen binding fragment of the antibody comprises:
   a) a heavy chain variable domain comprising CDR1, CDR2, and CDR3 of the amino acid sequence of SEQ ID NO: 1 and a light chain variable domain comprising CDR1, CDR2, and CDR3 of the amino acid sequence of SEQ ID NO: 2;
   b) a heavy chain variable domain comprising CDR1, CDR2, and CDR3 of the amino acid sequence of SEQ ID NO: 3 and a light chain variable domain comprising CDR1, CDR2, and CDR3 of the amino acid sequence of SEQ ID NO: 4, SEQ ID NO: 11, or SEQ ID NO: 12;
   c) a heavy chain variable domain comprising CDR1, CDR2, and CDR3 of the amino acid sequence of SEQ ID NO: 5 and a light chain variable domain comprising CDR1, CDR2, and CDR3 of the amino acid sequence of SEQ ID NO: 6; or
   d) a heavy chain variable domain comprising CDR1, CDR2, and CDR3 of the amino acid sequence of SEQ ID NO: 7 and a light chain variable domain comprising CDR1, CDR2, and CDR3 of the amino acid sequence of SEQ ID NO: 8.

2. The isolated polypeptide of claim 1, wherein the heavy chain variable domain comprises SEQ ID NO: 1 and the light chain variable domain comprises SEQ ID NO: 2.

3. The isolated polypeptide of claim 1, wherein the heavy chain variable domain comprises SEQ ID NO: 3 and the light chain variable domain comprises SEQ ID NO: 4, SEQ ID NO: 11, or SEQ ID NO: 12.

4. The isolated polypeptide of claim 1, wherein the heavy chain variable domain comprises SEQ ID NO: 5 and the light chain variable domain comprises SEQ ID NO: 6.

5. The isolated polypeptide of claim 1, wherein the heavy chain variable domain comprises SEQ ID NO: 7 and the light chain variable domain comprises SEQ ID NO: 8.

6. The isolated polypeptide of claim 1, wherein the antigen binding fragment of the antibody is chimeric, humanized, or a single chain antigen binding fragment.

7. The isolated polypeptide of claim 1, wherein the antigen binding fragment of the antibody is a Fab fragment, or a F(ab')2 fragment.

8. An isolated polynucleotide encoding the isolated polypeptide of claim 1.

9. A vector comprising the isolated polynucleotide of claim 8.

10. A cell comprising the vector of claim 9.

11. A method of treating a B cell-related disorder associated with BCMA expression, comprising administering the isolated polypeptide of claim 1.

12. The method of claim 11, wherein the B-cell related disorder is plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, small lymphocytic lymphoma, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy of undetermined significance.

13. The method of claim 11, wherein the B cell-related disorder is a B cell malignancy.

14. The method of claim 11, wherein the B cell-related disorder is a plasma cell malignancy.

15. The method of claim 14, wherein the plasma cell malignancy is multiple myeloma.

16. An isolated polynucleotide encoding the isolated polypeptide of claim 6.

17. A vector comprising the isolated polynucleotide of claim 16.

18. A cell comprising the vector of claim 17.

* * * * *